United States Patent
Ruijtenbeek et al.

(10) Patent No.: US 9,448,237 B2
(45) Date of Patent: Sep. 20, 2016

(54) MODIFIED TYROSINE AMINO ACIDS, PEPTIDES CONTAINING THEM, AND THEIR USE FOR DETECTING HYDROLASE ENZYME ACTIVITY

(75) Inventors: Robby Ruijtenbeek, Utrecht (NL); Jeroen van Ameijde, Utrecht (NL); Robertus Matthias Joseph Liskamp, Utrecht (NL)

(73) Assignees: PAMGENE B.V., 'S-Hertogenbosch (NL); UNIVERSITEIT UTRECHT HOLDING B.V., Utrecht (NL)

( * ) Notice: Subject to any disclaimer, the term of this patent is extended or adjusted under 35 U.S.C. 154(b) by 232 days.

(21) Appl. No.: 14/118,920

(22) PCT Filed: May 18, 2012

(86) PCT No.: PCT/EP2012/059293
§ 371 (c)(1),
(2), (4) Date: Nov. 20, 2013

(87) PCT Pub. No.: WO2012/159997
PCT Pub. Date: Nov. 29, 2012

(65) Prior Publication Data
US 2014/0155286 A1    Jun. 5, 2014

(30) Foreign Application Priority Data
May 20, 2011 (EP) ..................... 11166908

(51) Int. Cl.
| | | |
|---|---|---|
| C07K 2/00 | (2006.01) | |
| C07K 14/00 | (2006.01) | |
| G01N 33/573 | (2006.01) | |
| C07C 305/24 | (2006.01) | |
| C07F 9/12 | (2006.01) | |
| C12Q 1/42 | (2006.01) | |
| C07F 9/08 | (2006.01) | |

(52) U.S. Cl.
CPC ........... *G01N 33/573* (2013.01); *C07C 305/24* (2013.01); *C07F 9/08* (2013.01); *C07F 9/12* (2013.01); *C12Q 1/42* (2013.01)

(58) Field of Classification Search
None
See application file for complete search history.

(56) References Cited

U.S. PATENT DOCUMENTS

| | | | |
|---|---|---|---|
| 2010/0061936 A1 | 3/2010 | Shen | |
| 2010/0317831 A1 | 12/2010 | Lo | |

FOREIGN PATENT DOCUMENTS

JP    2006143669 A    6/2006

OTHER PUBLICATIONS

Yonemoto et al., Molecular and Cellular Biology (1987) 7(2), 905-913.*
Lopez et al., Neuroscience Letters (2005) 386, 78-81.*
Moss, Web version of Enzyme Nomenclature 1992, Academic Press, San Diego, available at http://www.chem.qmul.ac.uk/iubmb/enzyme/, accessed on Nov. 12, 2015.*
PCT International Search Report dated Aug. 21, 2012 in connection with PCT International Patent Application No. PCT/EP2012/059293, 4 pages.
PCT Notification Concerning Transmittal of International Preliminary Report on Patentability and Written Opinion of the International Searching Authority dated Sep. 26, 2013 in connection with PCT International Patent Application No. PCT/EP2012/059293, 7 pages.
Kalesh K A et al., entitled "Peptide-based activity-based probes (ABPs) for target-specific profiling of protein tyrosine phosphatases (PTPs)," Chemical Communications, vol. 46, No. 4, Jan. 1, 2010, pp. 589-591.
Shen K et al., entitled "Facile Incorporation of a Phosphatases Activity-Dependent Quinone Methide Generating Motif into Phosphotyrosine," Synthesis, No. 22, Sep. 23, 2009, pp. 3765-3768.
Hayashi A et al., entitled "Monoclonal antibodies specifically recognizing phosphorylated nonnatural amino acids for detecting phosphorylation in mammalian cells," Chemical Abstracts Service, Jun. 8, 2006, 2 pages.
Martin B et al., entitled "Use of fluorinated tyrosine phosphaes to probe the substrate specificity of the low molecular weight phosphatase activity of calcineurin," Journal of Biological Chemistry, vol. 260, No. 28, 1985, pp. 14932-14937.

* cited by examiner

*Primary Examiner* — Marcela M Cordero Garcia
*Assistant Examiner* — Catherine Mader
(74) *Attorney, Agent, or Firm* — Amster, Rothstein & Ebenstein LLP

(57) ABSTRACT

The present invention relates to a method and tools which allow the kinetic monitoring of hydrolase enzyme activity. The present invention also aims to provide synthetic peptides and peptide residues modified such that they can be used in assays for monitoring hydrolase enzyme activity, and preferably phosphatase activity. Also claimed are modified tyrosine amino acid derivatives of formula (IV), wherein Y is chosen from —$PO_y^{2-}$ with y equal to 2 or 3 and esters thereof, —$SO_z^-$ with z equal to 2 or 3 and esters thereof, a carbohydrate or carbohydrate derivatives; and; wherein $X_1$ and/or $X_2$ is selected from —$N_3$, —$NO_2$, —Cl, or —CN, —SCN, a $C_1$ to $C_8$ alkyl, or H, wherein either $X_1$ or $X_2$ is not H.

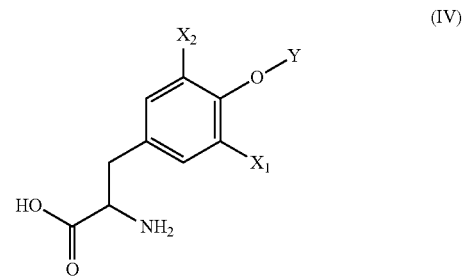

(IV)

5 Claims, 6 Drawing Sheets

MODIFIED TYROSINE AMINO ACIDS, PEPTIDES CONTAINING THEM, AND THEIR USE FOR DETECTING HYDROLASE ENZYME ACTIVITY

CROSS-REFERENCE TO RELATED APPLICATIONS

This application is a U.S. national stage entry under 35 U.S.C. §371 of PCT International Patent Application No. PCT/EP2012/059293, filed May 18, 2012, which claims priority to European Patent Application No. 11166908.1, filed May 20, 2011, the contents of which are incorporated herein by reference in their entirety.

FIELD OF THE INVENTION

The present invention relates to a method and tools which allow the kinetic monitoring of hydrolase enzyme activity. The present invention also aims to provide synthetic peptides and peptide residues modified such that they can be used in assays for monitoring hydrolase enzyme activity, and preferably phosphatase activity.

BACKGROUND OF THE INVENTION

The vital phosphorylation posttranslational modification is regulated by two classes of enzymes, the kinases which attach phosphate groups to proteins and the phosphatases which remove them. Phosphorylation plays a key role in cell signalling and thereby regulates a plethora of important cellular processes, such as apoptosis, division, differentiation, etc. Since deregulation of such processes is often implicated in serious diseases, e.g. cancer, diabetes and neurodegenerative diseases, it is no wonder that both enzyme families present important targets for drug research.

Of the two classes of enzymes, kinases have by far been most widely studied and targeted therapeutically, leading to several commercial drugs, e.g. Gleevec. Even though phosphatases are just as promising from a drug development perspective, the field has advanced much less. An important reason for this difference is the fact that in the kinase field many research tools are available for activity profiling, target identification, high throughput screening, etc. which is crucial for drug development. However, for phosphatases such tools are severely lacking.

A key problem in this respect is the fact that the product of the action of phosphatases on proteins or peptides is a natural amino acid (i.e. a tyrosine, threonine or serine residue) which is too small to be recognized by an antibody in a protein sequence-independent manner and may also already occur at different places in the protein substrate leading to a high and sequence dependent background signal. In fact, up to now the desired route—detection of formation of dephosphorylated protein or peptide—has been virtually impossible since the product of the phosphatase reaction is often tyrosine which is not a selective target for antibodies and which leads to interference with tyrosine residues elsewhere in the protein substrate. Furthermore, most current techniques only allow end-point determination instead of monitoring the reaction kinetics. From such a kinetic experiment much more information can be gained in one experiment about the phosphatase of interest.

An alternative which has been explored involves monitoring consumption of starting material since a number of detection methods for phosphorylated protein or peptide residues exist, for instance using radioactive phosphate isotopes, phosphate chelators or antibodies. However, such methods are hampered by the fact that measurement of a decreasing signal is inherently significantly less sensitive than monitoring an increasing signal. Furthermore, if the phosphate group is detected by binding to an antibody or chelator, these probes will obviously compete with the phosphatase for binding to the substrate leading to difficulties in interpretation of the resulting data.

Furthermore, in contrast to the kinases, existing detection strategies have not yet led to efficient and performant high-throughput phosphatase enzymatic activity assays e.g. microarray assays, which will be of the essence for diagnostic and therapeutic exploitation of these important enzymes.

Consequently, there remains a need for methods and tools that allow the monitoring and study of phosphatase activity, particularly in a high-throughput, parallel manner. This is required to move forward in e.g. phosphatase drug development and phosphatase-based diagnostics.

The present invention aims at providing methods and tools for detecting hydrolase enzyme activity in general and more specifically phosphatase activity.

SUMMARY OF THE INVENTION

The present invention provides methods and tools which allow the kinetic monitoring of hydrolase enzyme activity. Accordingly synthetic peptides and peptide residues are provided, wherein said peptides and peptide residues are modified such that they can be used in assays for monitoring hydrolase enzyme activity, and preferably phosphatase activity.

The present invention therefore provides a modified tyrosine amino acid according to formula IV

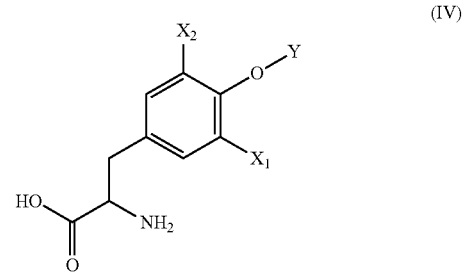

(IV)

wherein Y is chosen from —PO$_y^{2-}$ with y equal to 2 or 3 and esters thereof, —SO$_z^-$ with z equal to 2 or 3 and esters thereof, a carbohydrate or carbohydrate derivatives; and; wherein X$_1$ and/or X$_2$ is selected from —N$_3$, —NO$_2$, —Cl, or —CN, —SCN, a C$_1$ to C$_8$ alkyl, or H, wherein either X$_1$ or X$_2$ is not H.

Preferably Y is —PO$_3$ or —SO$_3$. More preferably X$_1$ is —NO$_2$.

The present invention further provides a synthetic peptide comprising between 2 and 100 amino acids, characterized therein that said peptide comprises at least one double modified tyrosine residue or tyrosine side chain according to formula I

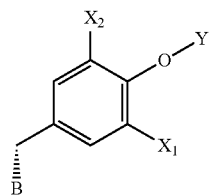

(I)

wherein B is the peptide backbone;
wherein Y is chosen from $-PO_y^{2-}$ with y equal to 2 or 3 and esters thereof, $-SO_z^-$ with z equal to 2 or 3 and esters thereof, a carbohydrate or carbohydrate derivatives; and;
wherein $X_1$ and/or $X_2$ is selected from $-N_3$, $-NO_2$, $-Cl$, or $-CN$, $-SCN$, a $C_1$ to $C_8$ alkyl, or H, wherein either $X_1$ or $X_2$ is not H.

Preferably Y is $-PO_3$ or $-SO_3$. Preferably $X_1$ is $-NO_2$.

The present invention further provides in the use of modified tyrosine amino acid according to formula IV wherein Y is chosen from $-PO_y^{2-}$ with y equal to 2 or 3 and esters thereof, $-SO_z^-$ with z equal to 2 or 3 and esters thereof, a carbohydrate or carbohydrate derivatives; and; wherein $X_1$ and/or $X_2$ is selected from $-N_3$, $-NO_2$, $-Br$, $-Cl$, $-I$, $-CN$, $-SCN$, a $C_1$ to $C_8$ alkyl, or H, wherein either $X_1$ or $X_2$ is not H, for detecting hydrolase enzyme activity, more preferably said hydrolase enzyme activity is chosen from EC 3.1, EC 3.2 or EC 3.3.

The present invention further provides in a method for the manufacturing of a double modified tyrosine monomer, comprising the steps of:

(a) modifying tyrosine monomers with a first protecting group on the amine residue, thereby obtaining a modified tyrosine monomer according to formula VII;

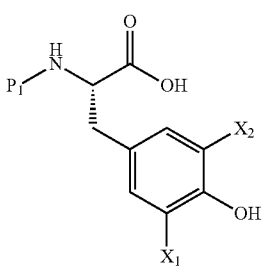

(VII)

wherein $X_1$ and/or $X_2$ is selected from $-N_3$, $-NO_2$, $-Br$, $-F$, $-Cl$, $-I$ or $-CN$, $-SCN$, $S(O)nR$, a $C_1$ to $C_8$ alkyl, or H, wherein either $X_1$ or $X_2$ is not H, and wherein $P_1$ is a first protecting group;

(b) modifying the modified tyrosine monomers obtained from step (a) by esterification of the carboxyl group, thereby obtaining a modified tyrosine monomer according to formula VIII;

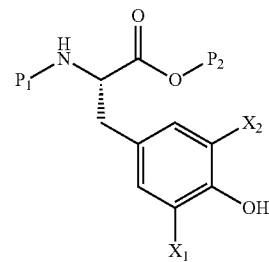

(VIII)

wherein $P_2$ is a second protecting group;
(c) modifying the modified tyrosine monomers obtained from step (b) by providing the remaining hydroxyl group with a functional group provided with secondary protecting groups, thereby obtaining a modified tyrosine monomer according to formula IX;

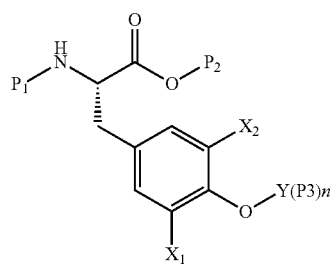

(IX)

wherein Y is chosen from $-NO_x$ with x equal to 1 or 2 and esters thereof, $-PO_y^{2-}$ with y equal to 2 or 3 and esters thereof, $-SO_z^-$ with z equal to 2 or 3 and esters thereof, a carbohydrate or carbohydrate derivatives; and;
wherein said Y group is provided with n $P_3$ groups, wherein $P_3$ is a third protecting group and n is an integer selected from 1, 2 or 3.

Preferably said protecting groups $P_1$, $P_2$ and $P_3$ are orthogonal and chosen from phthalimido, nitrobenzenesulphonyl, fluorenylmethyloxycarbonyl (Fmoc), tert-Butyloxycarbonyl (Boc), allyloxycarbonyl (Aloc), carboxybenzyl (Cbz), allyl, C1 to C8 alkyl, benzyl, (2-phenyl-2-trimethylsilyl)ethyl (PTMSE), phenyl, succinimidyl, pentafluorophenyl, pentachlorophenyl, 4-nitrophenyl, t-butyl, and/or 2-cyanoethyl.

The present invention further relates to a double modified tyrosine monomer according to formula IX or a peptoid thereof

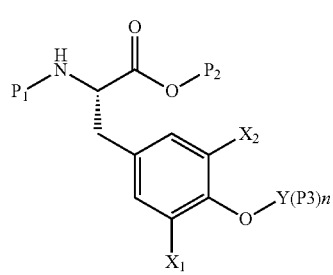

(IX)

wherein $P_1$, $P_2$ and $P_3$ are orthogonal protecting groups selected from phthalimido, nitrobenzenesulphonyl, Fmoc, Boc, Aloc, Cbz, allyl, C1 to C8 alkyl, benzyl, PTMSE, phenyl, succinimidyl, pentafluorophenyl, pentachlorophenyl, 4-nitrophenyl, t-butyl, and 2-cyanoethyl;

wherein $X_1$ and/or $X_2$ is selected from —$N_3$, —$NO_2$, —Cl, —CN, —SCN, a $C_1$ to $C_8$ alkyl, or H, wherein either $X_1$ or $X_2$ is not H;

wherein Y is chosen from —$PO_y^{2-}$ with y equal to 2 or 3 and esters thereof, —$SO_z^-$ with z equal to 2 or 3 and esters thereof, a carbohydrate or carbohydrate derivatives; and;

wherein said Y group is provided with n $P_3$ groups, wherein $P_3$ is a third protecting group and n is an integer selected from 1, 2 or 3.

More preferably $Y(P_3)n$ is according to formula XI

(XI)

wherein $P_3a$ and/or $P_3b$ are —H or a protecting group selected from benzyl, allyl, t-butyl, C1 to C8 alkyl, and/or 2-cyanoethyl; and wherein at least one of $P_3a$ or $P_3b$ is a protecting group.

The present invention further relates to the use of double modified tyrosine monomers according to the present invention for peptide synthesis.

The present invention further relates to a method for detecting hydrolase enzyme activity in a sample, said method comprising the step of:

contacting said sample with one or more modified tyrosine amino acids according to formula IV wherein Y is chosen from —$PO_y^{2-}$ with y equal to 2 or 3 and esters thereof, —$SO_z^-$ with z equal to 2 or 3 and esters thereof, a carbohydrate or carbohydrate derivatives; and; wherein $X_1$ and/or $X_2$ is selected from —$N_3$, —$NO_2$, —Br, —Cl, —I, —CN, —SCN, a $C_1$ to $C_8$ alkyl, or H, wherein either $X_1$ or $X_2$ is not H;

or contacting said sample with one or more synthetic peptides comprising between 2 and 100 amino acids, characterized therein that said peptide has incorporated therein at least one of said modified tyrosine amino acids detecting the product of the hydrolase enzyme activity on said amino acids or peptides, and optionally detecting the inhibition of hydrolase enzyme activity on said amino acids or peptides.

Preferably said hydrolase enzyme activity is phosphatase activity and wherein said synthetic peptides comprise at least one nitro phosphate tyrosine residue. Preferably said method is used for measuring the inhibition of said hydrolase enzyme activity.

The present invention further relates to an array comprising two or more synthetic peptides according to the present invention.

These and further aspects and embodiments are described in the following sections and in the claims.

Figure 1:
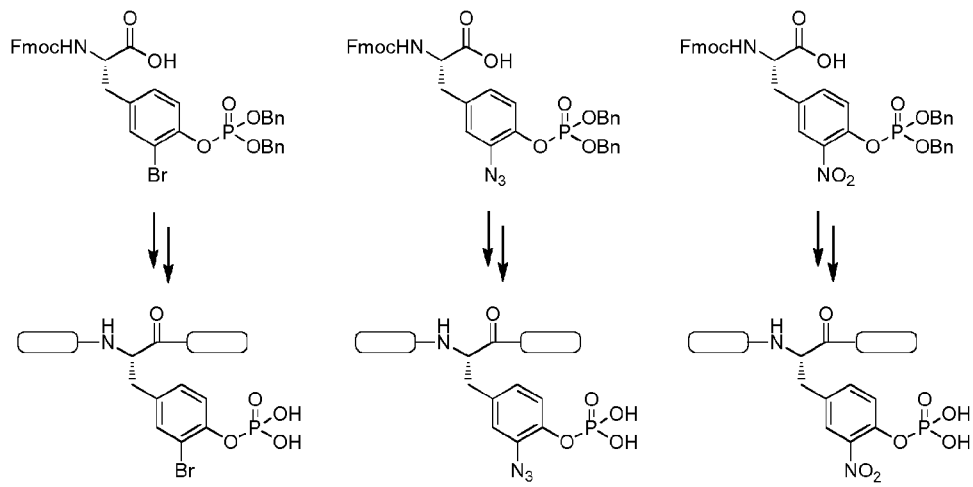
FIG. 1 provides double modified tyrosine monomers and resulting peptides.

A detailed description of the figures is provided in the examples.

DETAILED DESCRIPTION OF THE INVENTION

Before the present method and devices used in the invention are described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may be used in the practice or testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The terms "comprising", "comprises" and "comprised of" also include the term "consisting of". The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The present invention provides methods and tools which allow the kinetic monitoring of hydrolase enzyme activity. Accordingly synthetic peptides and peptide residues are provided, wherein said peptides and peptide residues are modified such that they can be used in assays for monitoring hydrolase enzyme activity, and preferably phosphatase activity. With peptide residues are meant peptide monomers or amino acids which according to the present invention have been modified such that they can be used in assays for monitoring hydrolase enzyme activity.

Preferably, in one embodiment of the present invention, synthetic peptides are provided wherein said peptides comprise at least one double modified tyrosine residue or tyrosine side chain which comprises at least two modifications, a first modification on a first position of the tyrosine residue provides a modification which is susceptible to the hydrolase enzyme activity, while a second modification is chosen such that sequence independent antibodies exist or may be raised, said antibodies being specific for the modified tyrosine residue after said residue has been subjected to hydrolase enzyme activity. The antibodies are therefore specific for the modified tyrosine residues where the first modification has been subjected to hydrolase enzyme activity.

For purposes of the present invention, and as used herein the term "hydrolase enzyme activity" refers to the activity of enzymes catalyze the hydrolysis of a chemical bond, thereby reaction product(s) are formed by a certain amount of hydrolase enzyme acting on a substrate during the course of the assay.

Specific hydrolase enzyme activity as intended by the present invention includes, but is not limited to the hydrolysis of ester bonds by esterases such as nucleases, phosphodiesterases, lipases or phosphatases, the hydrolysis of sugars by for instance DNA glycosylases, glycoside hydrolases or glycosidases, the hydrolysis of ether bonds by for instance epoxide hydrolase. Preferably said hydrolase enzyme activity is the hydrolysis of ester bonds by esterases such as nucleases, phosphodiesterases, lipases or phosphatases, and most preferably said hydrolase enzyme activity is phosphatase activity and/or protein phosphatase activity.

Phosphatase activity is referred to as the activity of protein phosphatases. A phosphatase is a generic name for all enzymes able to remove a phosphate group from a substrate by hydrolysing phosphoric acid monoesters into a phosphate ion and a molecule with a free hydroxyl group. This action is directly opposite to that of phosphorylases and kinases, which attach phosphate groups to their substrates by using energetic molecules like ATP. Protein phosphatases (PPs) are the primary effectors of dephosphorylation and can be grouped into three main classes based on sequence, structure and catalytic function. The largest class of PPs is the phosphoprotein phosphatase (PPP) family comprising PP1, PP2A, PP2B, PP4, PP5, PP6 and PP7, and the protein phosphatase $Mg^{2+}$- or $Mn^{2+}$-dependent (PPM) family, composed primarily of PP2C. The protein Tyrosine phosphatase (PTP) super-family forms the second group, and the aspartate-based protein phosphatases the third.

A protein phosphatase is a phosphatase enzyme that modifies other proteins by enzymatically removing phosphate groups from them. This process or activity is also referred to as dephosphorylation. Dephosphorylation can therefore be regarded as the process of the removing a phosphate group from a substrate. Dephosphorylation usually results in a functional change of the substrate by changing enzyme activity, cellular location, or association with other proteins. Up to 30% of all proteins may be modified by phosphatase activity, and phosphatases are known to regulate the majority of cellular pathways, especially those involved in signal transduction, the transmission of signals within the cell. The enzyme activity of a phosphatase involves removing a phosphate group from amino acids such as serine, threonine, tyrosine, histidine, aspartic acid and/or glutamic acid that have a free hydroxyl group. Most known phosphatases act on both serine and threonine, others act on tyrosine, and a number act on all serine, threonine and tyrosine. The protein phosphatase activity that can be monitored with the tools provided by the present invention is preferably directed to protein phosphatases acting towards tyrosines.

Protein phosphatases are distinguished by their ability to dephosphorylate substrates on discrete sequences. These sequences can be determined by sequencing the amino acids around the dephosphorylation sites and are usually distinct for each type of protein phosphatase.

Because protein phosphatases have profound effects on a cell, their activity is highly regulated. Phosphatases are turned on or off by for instance phosphorylation, by binding of activator proteins or inhibitor proteins, or small molecules, or by controlling their location in the cell relative to their substrates. Deregulated phosphatase activity is a frequent cause of disease, particularly cancer, where phosphatases regulate many aspects that control cell growth, movement and death. Therefore monitoring the protein phosphatase activity in tissues can be of great importance and a large amount of information can be obtained when comparing the phosphatase activity of different tissue samples. However the accurate and continuous monitoring of phosphatase activity is not evident with the tools currently available.

As described in the present invention, the inventors have found that the use of double modified tyrosine residues allow the precise kinetic monitoring of hydrolase enzyme activity, and preferably phosphatase activity.

The present invention therefore provides a (double) modified tyrosine amino acid according to formula IV

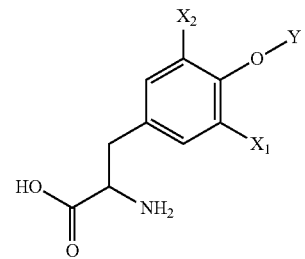

wherein Y is chosen from acetyl, a lipid, $—NO_x$ with x equal to 1 or 2 and esters or ethers thereof, $—PO_y$ with y equal to 2 or 3 and esters or ethers thereof, $—SO_z$ with z equal to 2 or 3 and esters or ethers thereof, a carbohydrate or carbohydrate derivatives; and;

wherein $X_1$ and/or $X_2$ is selected from $—N_3$, $—NO_2$, $—Br$, $—F$, $—Cl$, $—I$ or $—CN$, $—SCN$, $—S(O)nR$, a $C_1$ to $C_8$ alkyl, or H, wherein either $X_1$ or $X_2$ is not H. Preferably Y is $—PO_3$ or $—SO_3$. More preferably $X_1$ is $—NO_2$.

Carbohydrates, also referred to as saccharide, are organic compounds that consists only of carbon, hydrogen, and oxygen, usually with a hydrogen:oxygen atom ratio of 2:1 (as in water); and having a typical empirical formula $C_m(H_2O)_n$. The carbohydrates (saccharides) are divided into four chemical groupings: monosaccharides, disaccharides, oligosaccharides, and polysaccharides. More particularly, the carbohydrates referred to in the present invention are monosaccharides and more particularly, monosaccharides chosen from N-acetylglucosamine, N-acetylgalactosamine, fucose, glucose, galactose and mannose.

Single units of carbohydrates are also referred to as monosaccharides. These carbohydrates may undergo various reactions to form carbohydrate derivatives. Derivatives in case of carbohydrates refers to modifications of sugar molecules by addition substituents other than hydroxyl group. Amino sugars, acidic sugars, deoxy sugars, sugar alcohols, glycosylamines, and sugar phosphates are examples of carbohydrate derivatives.

The present invention also provides in double modified tyrosine amino acids according to formula IV

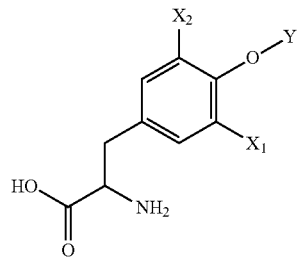

(IV)

wherein Y is chosen from —PO$_y^{2-}$ with y equal to 2 or 3 and esters thereof, —SO$_z^-$ with z equal to 2 or 3 and esters thereof, a carbohydrate or carbohydrate derivatives; and;

wherein $X_1$ and/or $X_2$ is selected from —N$_3$, —NO$_2$, —Cl, or —CN, —SCN, a $C_1$ to $C_8$ alkyl such as methyl or ethyl, or H, wherein either $X_1$ or $X_2$ is not H.

Preferably Y is chosen from —PO$_3$, —SO$_3$ or esters thereof and $X_1$ and/or $X_2$ is selected from —N$_3$, —NO$_2$, or —Br. More preferably Y is —PO$_3$ and $X_1$ and/or $X_2$ is selected from —N$_3$, —NO$_2$, or —Br. More preferably Y is —PO$_3$ and $X_1$ and/or $X_2$ is —NO$_2$. Alternatively, Y is —SO$_3$ and $X_1$ and/or $X_2$ is selected from —N$_3$, —NO$_2$, or —Br. More preferably Y is —SO$_3$ and $X_1$ and/or $X_2$ is —NO$_2$.

More preferably Y is chosen from —PO$_3$, —SO$_3$ or esters thereof and $X_1$ is selected from —N$_3$, —NO$_2$, or —Br. More preferably Y is —PO$_3$ and $X_1$ is selected from —N$_3$, —NO$_2$, or —Br. More preferably Y is —PO$_3$ and $X_1$ is —NO$_2$. Alternatively, Y is —SO$_3$ and $X_1$ is selected from —N$_3$, —NO$_2$ or, —Br. More preferably Y is —SO$_3$ and $X_1$ is —NO$_2$.

Preferably said double modified tyrosine amino acid is a phosphotyrosine provided with a 3-nitro, 3-azido or 3-bromo modification according to formula Va, Vb or Vc. Alternatively said double modified tyrosine amino acid is a sulphotyrosine provided with a 3-nitro, 3-azido or 3-bromo modification according to formula VIa, VIb or VIc.

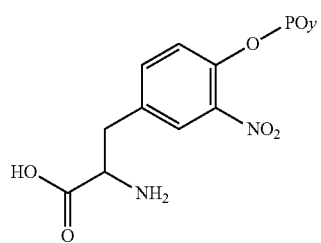

(Va)

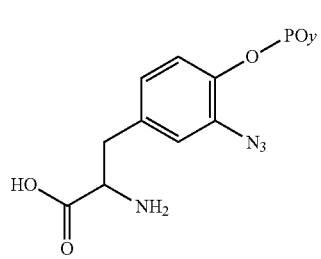

(Vb)

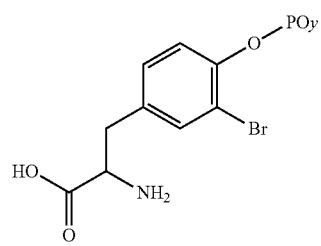

(Vc)

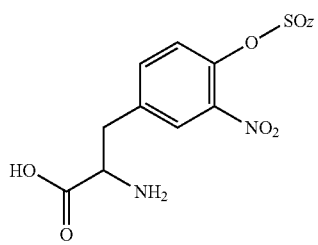

(VIa)

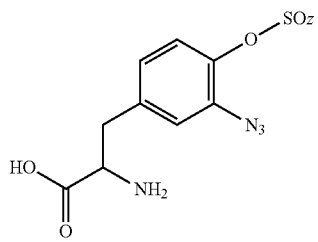

(VIb)

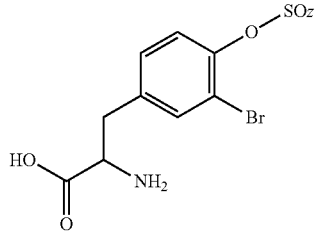

(VIc)

wherein y is equal to 2 or 3 and z is equal to 2 or 3, and preferably y and z being equal to 3.

The present invention further provides a synthetic peptide comprising between 2 and 100 amino acids, characterized therein that said peptide comprises at least one double modified tyrosine residue or tyrosine side chain according to formula I

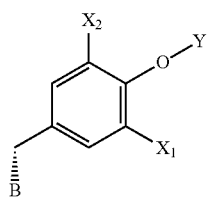

(I)

wherein B is the peptide or amino acid backbone;

wherein Y is chosen from acetyl, a lipid, —NO$_x$ with x equal to 1 or 2 and esters or ethers thereof, —PO$_y$ with y equal to 2 or 3 and esters or ethers thereof, —SO$_z$ with z equal to 2 or 3 and esters or ethers thereof, a carbohydrate or carbohydrate derivatives; and;

wherein $X_1$ and/or $X_2$ is selected from —$N_3$, —$NO_2$, —Br, —F, —Cl, —I or —CN, —SCN, S(O)nR, a $C_1$ to $C_8$ alkyl, or H, wherein either $X_1$ or $X_2$ is not H.

$X_1$ refers to a functional group on the 3 position of the tyrosine residue while $X_2$ refers to a functional group on the 5 position of the tyrosine residue.

Preferably Y is chosen from —$PO_3$, —$SO_3$ or esters thereof and $X_1$ and/or $X_2$ is selected from —$N_3$, —$NO_2$, or —Br. More preferably Y is —$PO_3$ and $X_1$ and/or $X_2$ is selected from —$N_3$, —$NO_2$, or —Br. More preferably Y is —$PO_3$ and $X_1$ and/or $X_2$ is —$NO_2$. Alternatively, Y is —$SO_3$ and $X_1$ and/or $X_2$ is selected from —$N_3$, —$NO_2$, or —Br. More preferably Y is —$SO_3$ and $X_1$ and/or $X_2$ is —$NO_2$.

More preferably Y is chosen from —$PO_3$, —$SO_3$ or esters thereof and $X_1$ is selected from —$N_3$, —$NO_2$, or —Br. More preferably Y is —$PO_3$ and $X_1$ is selected from —$N_3$, —$NO_2$, or —Br. More preferably Y is —$PO_3$ and $X_1$ is —$NO_2$. Alternatively, Y is —$SO_3$ and $X_1$ is selected from —$N_3$, —$NO_2$, or —Br. More preferably Y is —$SO_3$ and $X_1$ is —$NO_2$.

In another embodiment according to the present invention Y is —$PO_3$ or —$SO_3$.

In another embodiment according to the present invention $X_1$ is —$NO_2$.

Preferably said double modified tyrosine residue or tyrosine side chain is a phosphotyrosine provided with a 3-nitro, 3-azido or 3-bromo modification according to formula IIa, IIb or IIc. Alternatively said double modified tyrosine residue or tyrosine side chain is a sulphotyrosine provided with a 3-nitro, 3-azido or 3-bromo modification according to formula IIIa, IIIb or IIIc. B refers to the peptide backbone.

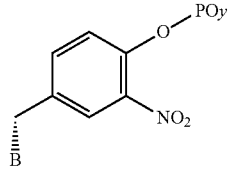

(IIa)

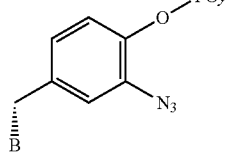

(IIb)

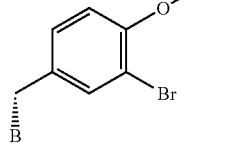

(IIc)

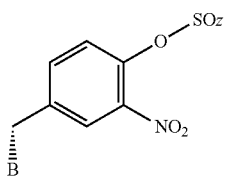

(IIIa)

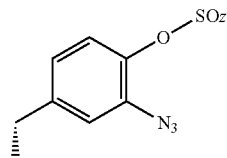

(IIIb)

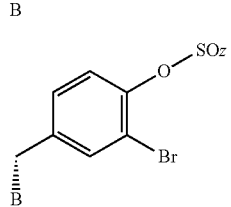

(IIIc)

wherein y is equal to 2 or 3 and z is equal to 2 or 3, and preferably y and z being equal to 3.

The synthetic peptides as referred to herein refer to short truncated proteins generally consisting of 2 to 100, preferably 5 to 50, more preferably 8 to 30 and even more preferably 13 to 18 naturally occurring or synthetic amino acids linked covalently through peptide bonds. The amino acids can be either those naturally occurring amino acids or chemically synthesized variants of such amino acids or modified forms of these amino acids which can be altered from their basic chemical structure by addition of other chemical groups which can be found to be covalently attached to them in naturally occurring compounds. Said synthetic peptides as referred to herein preferably relate to peptides comprising between 2 and 100 amino acids wherein said peptide comprises 1, 2, 3, 4 or 5 double modified tyrosine residues or tyrosine side chains according to the present invention. Typically said synthetic peptides are used as protein phosphatase substrates in assays for monitoring phosphatase activity. Each protein phosphatase substrate comprises, preferably one or more, sites that can be dephosphorylated by protein phosphatases with which they are put into contact with. Upon contacting the protein phosphatase substrates with a phosphatase or a multitude of phosphatases (for example phosphatases present in a sample) a method can be provided for the measurement of the activity of phosphatase enzymes present as these phosphatase enzymes will dephosphorylate, preferably one or more, of the phosphorylated sites on one or more protein phosphatase substrates.

As used herein, also a single amino acid, said amino acid being the double modified tyrosine according to the present invention may be used in the methods according to the present invention. The present invention therefore relates to a double modified tyrosine amino acid according to the present invention and also peptides comprising or incorporating said double modified tyrosine amino acid.

A person skilled in the art will appreciate that the double modified tyrosine residues as described herein can also be incorporated into proteins, peptides or peptide mimetics for the same purposes as described herein. As used herein "protein" or "peptide" refers to a polypeptide made of amino acids arranged in a linear chain and joined together by peptide bonds between the carboxyl and amino groups of adjacent amino acid residues. As used herein "peptide mimetics" refers to organic compounds which are structurally similar to peptides. The peptide mimetics are typically designed from existing peptides to alter the molecule's characteristics. Improved characteristics can involve, for example improved stability such as resistance to enzymatic degradation, or enhanced biological activity, improved affinity by restricted preferred conformations and ease of synthesis. Structural modifications in the peptidomimetic in comparison to a peptide, can involve backbone modifications as well as side chain modification.

The modification referred to as Y refers herein to the first modification on the first position of the tyrosine residue (on the hydroxyl group of the tyrosine residue). This first modification provides a modification which is susceptible to the hydrolase enzyme activity. The type of Y group depends on the type of hydrolase enzyme activity to be detected. For the monitoring of esterase activity, Y can for example be a lipid for monitoring lipases, —$PO_3$ for monitoring phosphatases, —$SO_3$ for monitoring sulfatases, phospho (di) esters for monitoring phosphor-esterases, sulpho (di) esters for monitoring sulpho-esterases, acetyl for monitoring deacetylases, a nitro group for monitoring denitrosylases, a carbohydrate for monitoring glycosidases . . . .

The modification referred to as $X_1$ and/or $X_2$ refers herein to the second modification which is chosen such that sequence independent antibodies exist or may be raised, said antibodies being specific for the tyrosine residue after said residue has been subjected to hydrolase enzyme activity. The antibodies are therefore specific for the tyrosine residues where the first modification has been subjected to hydrolase enzyme activity.

Another embodiment of the present invention relates to the use of any of the synthetic peptides according to the present invention, for detecting hydrolase enzyme activity.

In yet another embodiment, the present invention relates the use of a (double) modified tyrosine amino acid according to the present invention, wherein said hydrolase enzyme activity is chosen from EC 3.1, EC 3.2 or EC 3.3 and more specifically the hydrolysis of ester bonds (EC 3.1) by esterases such as nucleases, phosphodiesterases, lipases or phosphatases, the hydrolysis of sugars (EC 3.2) by for instance DNA glycosylases, glycoside hydrolases or glucosidases or the hydrolysis of ether bonds (EC 3.3) by for instance epoxide hydrolase. Preferably said hydrolase enzyme activity is the hydrolysis of ester bonds by esterases such as nucleases, phosphodiesterases, lipases or phosphatases, and most preferably said hydrolase enzyme activity is phosphatase activity and/or protein phosphatase activity.

More particularly of modified tyrosine amino acid according to formula IV wherein Y is chosen from —$PO_y^{2-}$ with y equal to 2 or 3 and esters thereof, —$SO_z^-$ with z equal to 2 or 3 and esters thereof, a carbohydrate or carbohydrate derivatives; and; wherein $X_1$ and/or $X_2$ is selected from —$N_3$, —$NO_2$, —Br, —Cl, —I, —CN, —SCN, a $C_1$ to $C_8$ alkyl, or H, wherein either $X_1$ or $X_2$ is not H, for detecting hydrolase enzyme activity, as defined above.

The present invention further relates to a method for the manufacturing of a double modified tyrosine monomer, comprising the steps of:

(a) modifying tyrosine monomers with a first protecting group on the amine residue, thereby obtaining a modified tyrosine monomer according to formula VII;

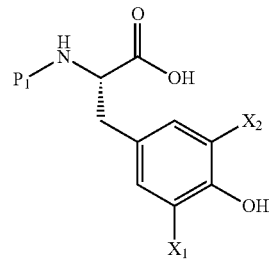

wherein $X_1$ and/or $X_2$ is selected from —$N_3$, —$NO_2$, —Br, —F, —Cl, —I or —CN, —SCN, S(O)nR, a $C_1$ to $C_8$ alkyl, or H, wherein either $X_1$ or $X_2$ is not H, preferably $X_1$ and/or $X_2$ is selected from —$N_3$, —$NO_2$ or —Br and more preferably —$NO_2$, most preferably $X_1$ is selected from —$N_3$, —$NO_2$, or —Br and more preferably —$NO_2$, and wherein $P_1$ is a first protecting group;

(b) modifying the modified tyrosine monomers obtained from step (a) by esterification of the carboxyl group, thereby obtaining a modified tyrosine monomer according to formula VIII;

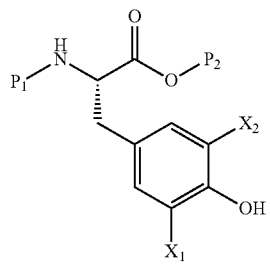

wherein $P_2$ is a second protecting group;

(c) modifying the modified tyrosine monomers obtained from step (b) by providing the remaining hydroxyl group with a functional group provided with secondary protecting groups, thereby obtaining a double modified tyrosine monomer according to formula IX;

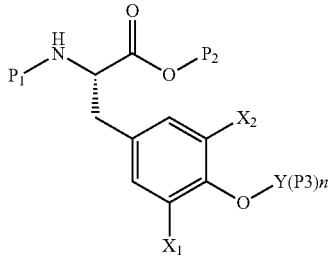

wherein Y is chosen from acetyl, a lipid, —$NO_x$ with x equal to 1 or 2 and esters or ethers thereof, —$PO_y$ with y equal to 2 or 3 and esters or ethers thereof, —$SO_z$ with z equal to 2 or 3 and esters or ethers thereof, a carbohydrate or carbohydrate derivatives; and;

wherein said Y group is provided with n $P_3$ groups, wherein $P_3$ is a third protecting group and n is an integer selected from 1, 2 or 3. When only one or two $P_3$ groups are provided the remaining positions are occupied by hydrogen or any type of suitable counterions.

More particularly, in the method step (c) Y is chosen from —NO$_x$ with x equal to 1 or 2 and esters thereof, —PO$_y^{2-}$ with y equal to 2 or 3 and esters thereof, —SO$_z^-$ with z equal to 2 or 3 and esters thereof, a carbohydrate or carbohydrate derivatives; and; said Y group is provided with n P$_3$ groups, wherein P$_3$ is a third protecting group and n is an integer selected from 1, 2 or 3.

The protecting groups P$_1$, P$_2$ and P$_3$ are chosen from the commonly known protecting groups known in the art such as for example trityl group, (2-phenyl-2-trimethylsilyl)ethyl (PTMSE) group, fluorenylmethyloxycarbonyl (-Fmoc), tert-Butyloxycarbonyl (-Boc), carboxybenzyl (-Cbz), -benzyl, -tertbutyl, or an alkyl-ester such as a methyl or ethyl ester, allyloxycarbonyl (Aloc), Phthalimido, trichloroethyl chloroformate (Troc), nitrobenzylsulphonyl or any other protecting groups known in the art.

The protecting group P$_1$ can be chosen from the commonly known protecting groups such the protecting groups described by Wuts, P. G. M. and Green, T. W. (Greene's Protective Groups in Organic Chemistry, 4th ed., John Wiley & Sons, Inc., 2007, Chapter 7) which is incorporated here by reference. Preferably P$_1$ is chosen from typical acid- or base-labile groups such as phthalimido, nitrobenzenesulphonyl, Fmoc, Boc, Aloc and/or Cbz, and more preferably chosen from Fmoc, Boc, Aloc and/or Cbz.

The protecting group P$_2$ can be chosen from the commonly known protecting groups such the protecting groups described by Wuts, P. G. M. and Green, T. W. (Greene's Protective Groups in Organic Chemistry, 4th ed., John Wiley & Sons, Inc., 2007, Chapter 5) which is incorporated here by reference. Preferably P$_2$ is chosen from allyl, C1 to C8 alkyl, benzyl, PTMSE, phenyl, succinimidyl, pentafluorophenyl, pentachlorophenyl, and/or 4-nitrophenyl.

The protecting group P$_3$ can be chosen from the commonly known protecting groups such the protecting groups described by Wuts, P. G. M. and Green, T. W. (Greene's Protective Groups in Organic Chemistry, 4th ed., John Wiley & Sons, Inc., 2007, Chapter 9) which is incorporated here by reference. Preferably P$_3$ is chosen from benzyl, H or a positively charged counterion, allyl, t-butyl, C1 to C8 alkyl, and/or 2-cyanoethyl.

Preferably the chosen protective groups P$_1$, P$_2$ and P$_3$ are orthogonal with respect to each other, meaning that each of these groups are separately removable. Non-limiting examples are for instance P$_1$ comprising a Cbz group, P$_3$ comprising tBu groups and P$_2$ comprising an allyl group. Orthogonal chosen protective groups are not essential but facilitate the synthesis of the modified tyrosine residues according to the present invention.

The chosen protective groups P$_1$, P$_2$ and P$_3$ are also chosen in function of substituent X$_1$ and/or X$_2$. For example, when Pac (phenacyl group), Troc, benzyl, trichloroethyl are used as protective group this is incompatible with X$_1$ and/or X$_2$ being a nitro-group as the chemical reaction required for removing the protective group will also reduce the nitro-group to an amine.

In general every combination is available according to e.g. Wuts, P. G. M. and Green, T. W. (Greene's Protective Groups in Organic Chemistry, 4th ed., John Wiley & Sons, Inc., 2007) where P$_1$, P$_2$ and P$_3$ are orthogonal with respect to deprotection conditions, and where said deprotection conditions are compatible with group X$_1$ and/or X$_2$.

Preferred combinations of orthogonal combinations of P$_1$/P$_3$ include but are not limited to Fmoc/benzyl, Fmoc/allyl, Boc/allyl, Boc/2-cyanoethyl, etc.

Preferred combinations also include but are not limited to [P$_1$/P$_2$/P$_3$]: [Fmoc/allyl/benzyl], [Boc/allyl/2-cyanoethyl], [Fmoc/tert-butyl/allyl], [Boc/TMSE/allyl], [Fmoc/allyl/tert-butyl], [Fmoc/allyl/TBDMS], Fmoc/benzyl/allyl, Fmoc/ethyl/allyl, Fmoc/allyl/trityl, Boc/allyl/benzyl, etc.

In another embodiment, the present invention regards a method according to the present invention wherein said protecting groups P$_1$, P$_2$ and P$_3$ are orthogonal and chosen from phthalimido, nitrobenzenesulphonyl, Fmoc, Boc, Aloc, Cbz, allyl, C1 to C8 alkyl, benzyl, PTMSE, phenyl, succinimidyl, pentafluorophenyl, pentachlorophenyl, 4-nitrophenyl, benzyl, H, or a positively charged counterion, allyl, t-butyl, C1 to C8 alkyl and/or 2-cyanoethyl.

The present invention further relates to a double modified tyrosine monomer according to formula IX or a peptoid thereof, wherein X$_1$ and/or X$_2$ is selected from —N$_3$, —NO$_2$, —Br, —F, —Cl, —I or —CN, —SCN, S(O)nR, a C$_1$ to C$_8$ alkyl, or H, wherein either X$_1$ or X$_2$ is not H, preferably X$_1$ and/or X$_2$ is selected from —N$_3$, —NO$_2$, or —Br and more preferably —NO$_2$, most preferably X$_1$ is selected from —N$_3$, —NO$_2$, or —Br and more preferably —NO$_2$, wherein P$_1$ is a first protecting group, preferably chosen from typical acid- or base-labile groups such as phthalimido, nitrobenzenesulphonyl, Fmoc, Boc, Aloc and/or Cbz, and more preferably chosen from Fmoc, Boc, Aloc and/or Cbz;

wherein P$_2$ is a secondary protecting group preferably selected from allyl, C1 to C8 alkyl, benzyl, PTMSE, phenyl, succinimidyl, pentafluorophenyl, pentachlorophenyl, and/or 4-nitrophenyl;

wherein Y is chosen from acetyl, a lipid, —NO$_x$ with x equal to 1 or 2 and esters or ethers thereof, —PO$_y$ with y equal to 2 or 3 and esters or ethers thereof, —SO$_z$ with z equal to 2 or 3 and esters or ethers thereof, a carbohydrate or carbohydrate derivatives; and;

wherein said Y group is provided with n P$_3$ groups, wherein n is an integer selected from 1, 2 or 3 and P$_3$ is a third protecting group preferably chosen from benzyl, H or a positively charged counterion, allyl, t-butyl, C1 to C8 alkyl and/or 2-cyanoethyl.

With a peptoid is meant a class of peptidomimetics whose side chains are appended to the nitrogen atom of the peptide backbone, rather than to the α-carbons. In peptoids the side chain is connected to the nitrogen of the peptide backbone, instead of the α-carbon as in peptides. Notably, peptoids lack the amide hydrogen which is responsible for many of the Secondary structure elements in peptides and proteins. Peptoids were first described by Reyna et al (U.S. Pat. No. 5,811,387 which is incorporated herein by reference) to mimic protein/peptide products to aid in the discovery of protease-stable small molecule drugs. Preferably with peptoid is meant a peptoid according to formula X

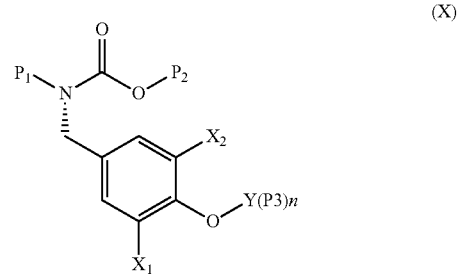

(X)

wherein X$_1$ and/or X$_2$ is selected from —N$_3$, —NO$_2$, —Br, —F, —Cl, —I or —CN, —SCN, S(O)nR, a C$_1$ to C$_8$ alkyl, or H, wherein either X$_1$ or X$_2$ is not H, preferably X$_1$ and/or $X_2$ is selected from —$N_3$, —$NO_2$, or —Br and more preferably —$NO_2$, most preferably $X_1$ is selected from —$N_3$, —$NO_2$, or —Br and more preferably —$NO_2$, and wherein $P_1$ is a first protecting group and $P_2$ is a second protecting group; and wherein Y is chosen from —$NO_x$ with x equal to 1 or 2 and esters thereof, —$PO_y^{2-}$ with y equal to 2 or 3 and esters thereof, —$SO_z^-$ with z equal to 2 or 3 and esters thereof, a carbohydrate or carbohydrate derivatives; and; said Y group is provided with n $P_3$ groups, wherein $P_3$ is a third protecting group and n is an integer selected from 1, 2 or 3. In another embodiment, the present invention relates to a double modified tyrosine monomer according to the present invention, wherein said protecting groups $P_1$, $P_2$ and $P_3$ are orthogonal and chosen from phthalimido, nitrobenzenesulphonyl, Fmoc, Boc, Aloc, Cbz, allyl, C1 to C8 alkyl, benzyl, PTMSE, phenyl, succinimidyl, pentafluorophenyl, pentachlorophenyl, 4-nitrophenyl, benzyl, H or a positively charged counterion, allyl, t-butyl, C1 to C8 alkyl and/or 2-cyanoethyl. More particularly, said double modified tyrosine monomer is a monomer according to the present invention wherein $X_1$ and/or $X_2$ is selected from —$N_3$, —$NO_2$, —Cl, —CN, —SCN, a $C_1$ to $C_8$ alkyl, or H, wherein either $X_1$ or $X_2$ is not H; wherein Y is chosen from —$PO_y^{2-}$ with y equal to 2 or 3 and esters thereof, —$SO_z^-$ with z equal to 2 or 3 and esters thereof, a carbohydrate or carbohydrate derivatives; and; wherein said Y group is provided with n $P_3$ groups, wherein $P_3$ is a third protecting group and n is an integer selected from 1, 2 or 3.

In another embodiment, the present invention relates to a double modified tyrosine monomer according to the present invention, wherein $Y(P_3)n$ is according to formula XI

(XI)

wherein $P_3a$ and/or $P_3b$ are chosen from —H or a protecting group such as benzyl, H or a positively charged counterion, allyl, t-butyl, C1 to C8 alkyl and/or 2-cyanoethyl; and; wherein preferably at least one of $P_3a$ or $P_3b$ is a protecting group. More particularly, $P_3a$ and/or $P_3b$ are —H or a protecting group selected from benzyl, allyl, t-butyl, C1 to C8 alkyl and/or 2-cyanoethyl; and wherein at least one of $P_3a$ or $P_3b$ is a protecting group.

The present invention further relates to the use of double modified tyrosine monomers according to the present invention for peptide synthesis.

Peptide synthesis as used herein refers to the production of peptides, multiple amino acids linked via peptide bonds. Peptides are synthesized by coupling the carboxyl group or C-terminus of one amino acid to the amino group or N-terminus of another. In the art a multitude of peptide synthesis techniques are available, all making use of amino-acid monomers which have been modified to be used in the peptide synthesis technique. A skilled person will appreciate that the double modified tyrosine monomers according to the present invention are also suitable for use in peptide synthesis technology, such as automated solid phase peptide synthesis SPPS, spot synthesis (Jerini), combinatorial synthesis of peptide libraries . . . .

The present invention also relates according to another embodiment to a method for detecting hydrolase enzyme activity in a sample, said method comprising the step of:

contacting said sample with one or more modified tyrosine amino acids or synthetic peptides according to the present invention wherein said synthetic peptides comprise between 2 and 100 amino acids, characterized therein that said synthetic peptides comprise at least one double modified tyrosine residue according to formula I wherein B is the peptide backbone;

wherein Y is chosen from acetyl, a lipid, —$NO_x$ with x equal to 1 or 2 and esters or ethers thereof, —$PO_y$ with y equal to 2 or 3 and esters or ethers thereof, —$SO_z$ with z equal to 2 or 3 and esters or ethers thereof, a carbohydrate or carbohydrate derivatives; preferably chosen from —$PO_3$, —$SO_3$ or esters thereof; and;

wherein $X_1$ and/or $X_2$ is selected from —$N_3$, —$NO_2$, —Br, —F, —Cl, —I or —CN, —SCN, S(O)nR, a $C_1$ to $C_8$ alkyl, or H, wherein either $X_1$ or $X_2$ is not H, and preferably from —$N_3$, —$NO_2$ or —Br; and;

detecting the product of the hydrolase enzyme activity on said peptides, preferably using labelled antibodies specifically binding to modified tyrosine residues after being subjected to the hydrolase enzyme activity.

More particularly, said sample is contacted with one or more modified tyrosine amino acids according to formula IV wherein Y is chosen from —$PO_y^{2-}$ with y equal to 2 or 3 and esters thereof, —$SO_z^-$ with z equal to 2 or 3 and esters thereof, a carbohydrate or carbohydrate derivatives; and; wherein $X_1$ and/or $X_2$ is selected from —$N_3$, —$NO_2$, —Br, —Cl, —I, —CN, —SCN, a $C_1$ to $C_8$ alkyl, or H, wherein either $X_1$ or $X_2$ is not H; or wherein said sample is contacted with one or more synthetic peptides comprising between 2 and 100 amino acids, characterized therein that said peptide has incorporated therein at least one of said modified tyrosine amino acids.

With the product of the hydrolase enzyme activity, as referred herein, is meant the modified tyrosine residue according to the present invention wherein the —O—Y bond has been subjected to hydrolytic activity, resulting in an —OH group, the modified tyrosine residue thereby only retaining the $X_1$ and/or $X_2$ residue.

Preferably in the present method the sample is contacted with one or more synthetic peptides comprising between 2 and 100 amino acids and preferably between 5 and 50 amino acids, and/or single amino acids according to the present invention, provided that the synthetic peptides or amino acids comprise at least one double modified tyrosine residue according to formula I.

As used in the present invention, the term "sample" refers to any type of sample providing hydrolytic activity and preferably a sample comprising one or more hydrolases as used in the present invention. Said sample may be obtained from various sources including solutions, extracts or lysates obtained from environmental samples, bodily fluids, cell cultures etc. such as a cell lysate, a cell extract, tissue sample, cerebrospinal fluid, urine, blood, plasma, serum, saliva, bone marrow, bacterial extracts . . . .

Said sample may be a sample containing a purified hydrolase enzyme such as a phophatase.

Said sample may be a solution containing one or more hydrolases or a cell-lysate of a cell-line containing overexpressed or endogenous expressed one or more hydrolases.

Said sample may also be obtained from an organism (patient) such as human or from components (e.g. tissue or cells) of such an organism. Said sample may be obtained from a patient diagnosed with cancer and needs to be derived from the tumor tissue of said patient. Exemplary, said sample is a tumor tissue biopsy, fine needle biopsy, fine needle aspiration biopsy, core needle biopsy, vacuum assisted biopsy, open surgical biopsy or material from a resected tumor. Said sample is thereby referred to as a 'clinical sample' which is a sample derived from a cancer patient. Said tumor tissue sample is may also be a fresh or a fresh frozen sample.

Preferably, said sample refers to a lysate obtained from for example a tumor tissue obtained through tumor tissue biopsy, fine needle biopsy, fine needle aspiration biopsy, core needle biopsy, open surgical biopsy or material from a resected tumor. Alternatively said sample may be obtained from specific tumor cell lines and in particular cell lysates thereof. Alternatively said sample may be derived from a tumor sample that has been cultured in vitro for a limited period of time.

In a preferred embodiment of the present invention said sample is a sample that has undergone a preparation step prior to the steps according to the method of the present invention. Preferably said preparation step is a step where the protein hydrolases, preferably phosphatases, present in said sample are released from the tissue by lysis. Additionally the hydrolases, preferably phosphatases in the sample may be stabilized, maintained, enriched or isolated, and the measurement of the hydrolase, preferably phosphatase activity as performed in step (a) occurs on the enriched or isolated protein hydrolase, preferably phosphatase sample. By first enriching protein hydrolases, preferably phosphatases, in the sample or isolating protein hydrolases, preferably phosphatases, from the sample the subsequent measurement of the hydrolase, preferably phosphatase activity will occur in a more efficient and reliable manner. Also the clarity and intensity of the obtained signal will be increased as certain contaminants, or interferants are being removed during the enriching or isolating step.

It should be noted that for the measurement of the protein hydrolase, preferably phosphatase activity, other additional compounds such as kinase inhibitors, phophatase inhibitors, general reducing agents, etc. may be added. These compounds are not required and depend mainly on the type of sample that is used for performing the assay. Alternatively, the hydrolysis of the protein hydrolase substrates, preferably phosphatase substrates, can be performed in the absence of exogenous compounds.

The hydrolysis of each of the protein hydrolase substrates, preferably phosphatase substrates, can be monitored using typical methods known in the art. The hydrolysis of the protein hydrolase substrates, preferably phosphatase substrates, provided with the tyrosine residues according to the present invention, result in a detectable signal. This signal can be either attributed to a reaction of the substrates with antibodies, but also other measurement methods are available such as for instance measuring mass differences using mass spectrometry or the direct measurement of the hydrolysis since the product of the reaction contains a nitrophenol moiety which absorbs at 405 nm. These alternative detection techniques not requiring antibodies are therefore available as well.

In determining the interaction of the sample with the protein hydrolase substrates, preferably phosphatase substrates, the signal is the result of the interaction of the substrates with a detectably labelled molecule capable of binding to the substrates subjected to the hydrolysis. For the latter, the molecule that specifically binds to the substrates of interest (e.g., antibody) can be detectably labelled by virtue of containing an atom (e.g., radionuclide), molecule (e.g., fluorescein), or enzyme or particle or complex that, due to a physical or chemical property, indicates the presence of the molecule. A molecule may also be detectably labelled when it is covalently bound to or otherwise associated with a "reporter" molecule (e.g., a biomolecule such as an enzyme) that acts on a substrate to produce a detectable atom, molecule or other complex.

Detectable labels suitable for use in the present invention include any composition detectable by spectroscopic, photochemical, biochemical, immunochemical, electrical, optical or chemical means. Labels useful in the present invention include biotin for staining with labelled avidin or streptavidin conjugate, magnetic beads (e.g., Dynabeads'), fluorescent dyes (e.g., fluorescein, fluorescein-isothiocyanate (FITC), Texas red, rhodamine, green fluorescent protein, enhanced green fluorescent protein, lissamine, phycoerythrin, Cy2, Cy3, Cy3.5, Cy5, Cy5.5, Cy7, FluorX [Amersham], SYBR Green I & II [Molecular Probes], and the like), radiolabels (e.g., 3H, 125I, 35S, 14C, or 32P), enzymes (e.g., hydrolases, particularly phosphatases such as alkaline phosphatase, esterases and glycosidases, or oxidoreductases, particularly peroxidases such as horse radish peroxidase, and the like), substrates, cofactors, chemilluminescent groups, chromogenic agents, and colorimetric labels such as colloidal gold or coloured glass or plastic (e.g., polystyrene, polypropylene, latex, etc.), protein particles or beads.

Means of detecting such labels are well known to those of skill in the art. Thus, for example, chemiluminescent and radioactive labels may be detected using photographic film or scintillation counters, and fluorescent markers may be detected using a photodetector to detect emitted light (e.g., as in fluorescence-activated cell sorting). Enzymatic labels are typically detected by providing the enzyme with a substrate and detecting a coloured reaction product produced by the action of the enzyme on the substrate. Colorimetric labels are detected by simply visualizing the coloured label. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the colour associated with the label. Fluorescence resonance energy transfer has been adapted to detect binding of unlabeled ligands, which may be useful on arrays.

In a particular embodiment of the present invention the response of the substrates to the sample is determined using detectably labelled antibodies; more in particular fluorescently labelled antibodies, and more preferably using fluorescently labelled anti-nitrotyrosine antibodies. The use of fluorescently labelled antibodies in the method of the present invention, allows real-time or semi real-time determination of the hydrolase activity and accordingly provides the possibility to express the hydrolase activity as the initial velocity of hydrolase derived from the activity over a certain period of incubation of the sample on the substrates.

The present invention also relates in another embodiment to a method according to the present invention wherein said hydrolase enzyme activity is phosphatase activity and wherein said synthetic peptides comprise at least one nitro phosphate tyrosine residue.

The present invention also relates in another embodiment to a method according to the present invention for measuring the inhibition of said hydrolase enzyme activity.

The present invention further relates to an array comprising two or more synthetic peptides according to the present invention.

More particularly, said array comprises two or more synthetic peptides having incorporated at least one modified tyrosine amino acid according to formula IV wherein Y is chosen from $-PO_y^{2-}$ with y equal to 2 or 3 and esters thereof, $-SO_z^-$ with z equal to 2 or 3 and esters thereof, a carbohydrate or carbohydrate derivatives; and; wherein $X_1$ and/or $X_2$ is selected from $-N_3$, $-NO_2$, $-Br$, $-Cl$, $-I$, $-CN$, $-SCN$, a $C_1$ to $C_8$ alkyl, or H, wherein either $X_1$ or $X_2$ is not H.

For measuring the hydrolase activity of the sample a large variety of methods and formats are known in the art. The hydrolase activity can for example be measured using ELISA and multiplex ELISA techniques, blotting methods, mass spectrometry, capillary electrophoresis, bead arrays, macroarrays, microarrays or any other method known in the art. Depending on the type of hydrolase activity measurement method the solid support on which the proteins, peptides or peptide mimetics are fixed may vary. Whereas in ELISA the substrates are attached to the surface of the microtiterplates, in microarrays the substrates are immobilized on and/or in the microarray substrate. Alternatively the substrates are synthesized in-situ direct on the microarray substrate.

In a preferred embodiment of the present invention the substrates are immobilized on an array, and preferably a microarray of substrates wherein the substrates are immobilized onto a solid support or another carrier. The immobilization can be either the attachment or adherence of two or more substrate molecules to the surface of the carrier including attachment or adherence to the inner surface of said carrier in the case of e.g. a porous or flow-through solid support.

In a preferred embodiment of the present invention, the array of substrates is a flow-through array. The flow-through array as used herein could be made of any carrier material having oriented through-going channels as are generally known in the art, such as for example described in PCT patent publication WO 01/19517. Typically the carrier is made from a metal oxide, glass, silicon oxide or cellulose. In a particular embodiment the carrier material is made of a metal oxide selected from the group consisting of zinc oxide, zirconium oxide, tin oxide, aluminium oxide, titanium oxide and thallium; in a more particular embodiment the metal oxide consists of aluminium oxide.

Accordingly, in a further embodiment of the present invention said array is a Pamchip®.

The current invention describes methods and tools for use in technological platforms for the high throughput study of phosphatase activity, which will be of vital importance for further opening up the phosphatases as a drug target. In the methods presented here, a chemically double modified phosphotyrosine residue is incorporated into phosphatase substrate peptides which are preferably immobilized onto an aluminium oxide microarray surface in discrete spots. The chemical modification is selected so that sequence independent antibodies to the dephosphorylated modified amino acid resulting from phosphatase activity exist or may be raised. Since the resulting residue has been chemically modified, it does not occur elsewhere in the sequence and therefore does not suffer from increased background signal. Furthermore, using this methodology it is possible to monitor product formation which can be performed sensitively and does not involve probes competing for the substrate with the phosphatase under investigation.

Several chemical modifications of phosphotyrosine have been envisaged. As specific examples in the present invention the 3-nitro, 3-azido and 3-bromo modification are described. In the present examples the substituents are always introduced at the 3-position as it is chemically the most convenient position to introduce a substituent and a substituent on this position seems to be tolerated by phosphatases. Syntheses of tyrosines substituted at the 2-position may be envisaged and for example 3,5-dinitro phosphotyrosine may be prepared as well in a similar way to the synthesis described in the present patent application.

The present invention is hereafter exemplified by the illustration of particular, non-limiting examples.

EXAMPLES

Example 1

Modified Tyrosine Monomers and Method for the Synthesis

The present example provides the preparation of double modified tyrosine residues with suitable protecting groups for solid phase peptide synthesis (FIG. 1).

In this case the base-labile Fmoc-group was used in combination with acid-labile benzyl protection of the phosphate group. However, other protection strategies may be envisaged as well, e.g. Boc- or Cbz-protection of the amino group, or alternative phosphate protection such as tBu-, Me- or Et-esters.

Figure 2:
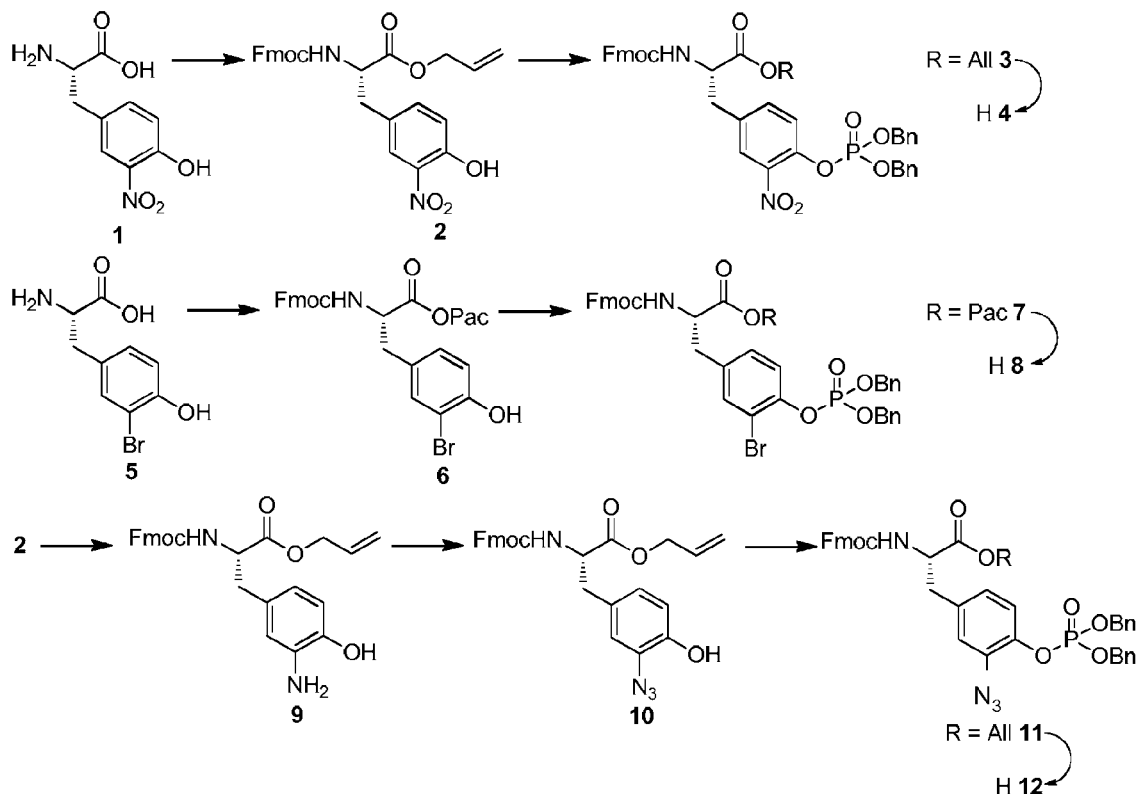
FIG. 2 provides a synthesis scheme for double modified tyrosine monomers.
Figure 3:
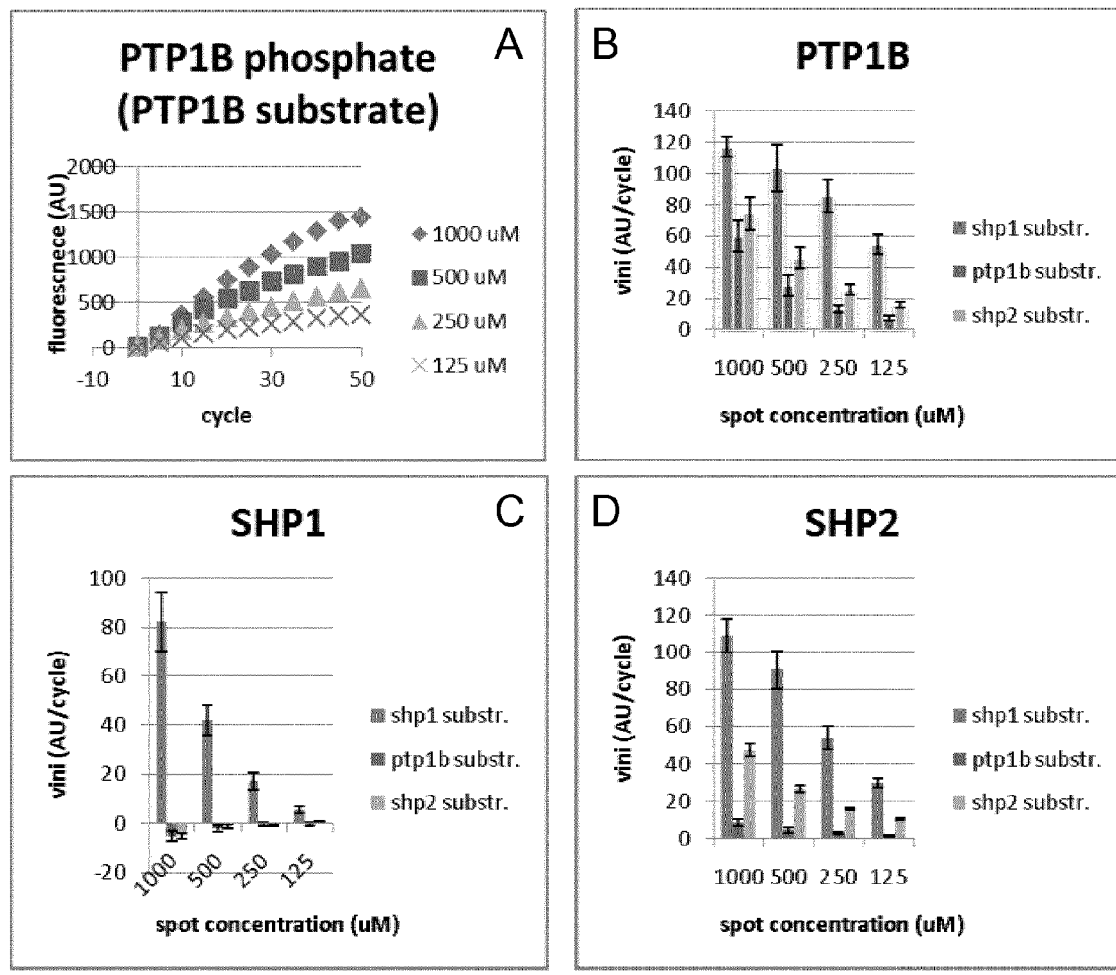
FIG. 3 provides kinetic data using 3-nitro derivatives.

The syntheses of the monomers are shown in FIG. 2. For the 3-nitro derivative, 3-nitrotyrosine was furnished with an Fmoc-group using Fmoc-OSu and DiPEA, followed by allylation with allyl bromide and DiPEA, leading to crystalline 2 in a more than 90% yield. The protected phosphate group was introduce using dibenzyl diisopropylphosphoramidate and tetrazole, immediately followed by oxidation with mCPBA, leading to formation of fully protected derivative 3 after purification by column chromatography. Finally, the allyl group was removed under Pd° catalysis in a more than 90% yield.

The 3-azido derivative was prepared from protected 3-nitrotyrosine 2, by reducing the nitro group with Zn and acetic acid leading to 9 in 57% yield. Subsequent diazo transfer using triflic azide and copper sulfate led to formation of 10, after which the synthesis was continued as described for the nitrotyrosine monomer, affording 3-azido monomer 12.

The 3-bromo derivative was synthesized from known 3-bromotyrosine 5 which was protected with Fmoc- and Pac-protecting groups using Fmoc-OSu and Pac-Br respectively. The phosphate group was introduced as described above leading to fully protected derivative 7 which was subjected to Zn under acidic conditions to remove the Pac-ester, yielding 3-bromo monomer 8.

Example 2

Phosphatase Assays

The present example provides non-limiting examples of assays for monitoring phosphatase activity. The monomers according to example 1 were incorporated into phosphatase substrate peptides according to routine Fmoc/tBu solid phase peptide synthesis protocols. The double modified monomers were coupled using 2 eq of monomer in the presence of coupling reagent BOP (Benzotriazole-1-yl-oxy-tris-(dimethylamino)-phosphonium hexafluorophosphate) and base DiPEA, applying a one hour coupling time. All resulting peptides (Table 1) were prepared in good yields (typically more than 93% per step) and could be conveniently purified by preparative reversed phase HPLC.

TABLE 1

Peptide sequences.

| SEQ. ID. NO | Sequence: | Derived from: | Target phosphatase: |
|---|---|---|---|
| 1 | H-CGSAAP-(3-NO$_2$-pY)-LKTK-NH$_2$ | Stat3 | PTP1B |
| 2 | H-CGDEGIH-(3-NO$_2$-pY)-SELI-NH$_2$ | Siglec2 | SHP1 |
| 3 | H-CGPQDKE-(3-NO$_2$-pY)-YKVK-NH$_2$ | Jak2 | SHP2 |
| 4 | H-CGSAAP-(3-N$_3$-pY)-LKTK-NH$_2$ | Stat3 | PTP1B |
| 5 | H-CDADE-(3-Br-pY)-LIPQQG-NH$_2$ | EGFR | PTP1B |

Figure 4:
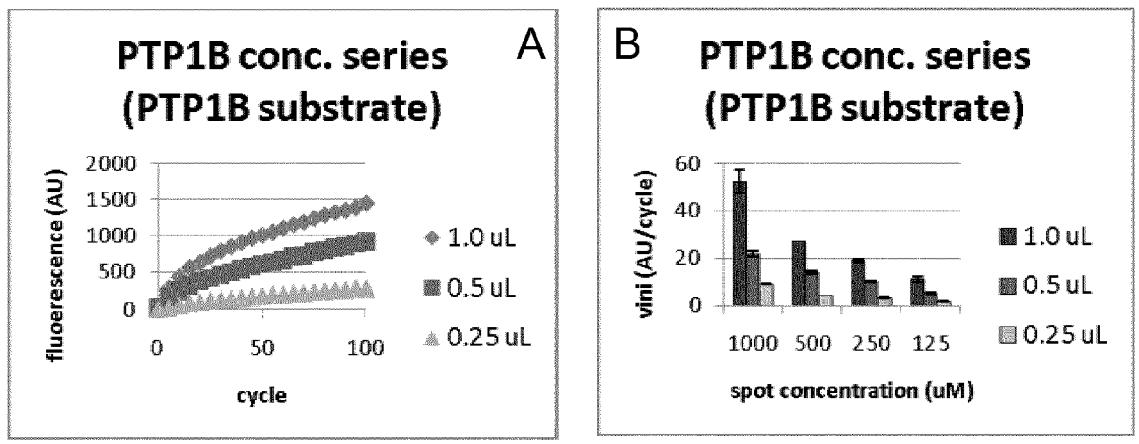
FIG. 4 provides enzyme concentration data.

The peptides were spotted onto a microarray surface in a concentration series (1000, 500, 250 and 125 μM). For studying the nitro derivatives, the resulting microarrays were treated with buffered solutions of the phosphatase of interest (typically 20-100 ng) in the presence of BSA and an anti-nitrotyrosine antibody (in this case monoclonal antibodies 39B6 and HM11 were used, but several others are commercially available: 2A8.2, 2A12, 11C2, 1A6, CC22.8C7.3, 7A12AF6 and polyclonal antibodies.) Pictures were taken at regular intervals using a fluorescence microscope. Strong signals could be observed under these conditions which increased over time allowing kinetic measurement. From the resulting images progress curves and initial velocities could be derived (FIG. 3A and FIG. 4A), which clearly demonstrated substrate concentration dependence as expected for an enzymatic reaction. In FIG. 3A to D each cycle represents an incubation of 30 seconds. As expected, the signal obtained was dependent on the enzyme concentration (FIG. 3B, C and D) and the amount of immobilized substrates as well (FIG. 4B).

Figure 5:
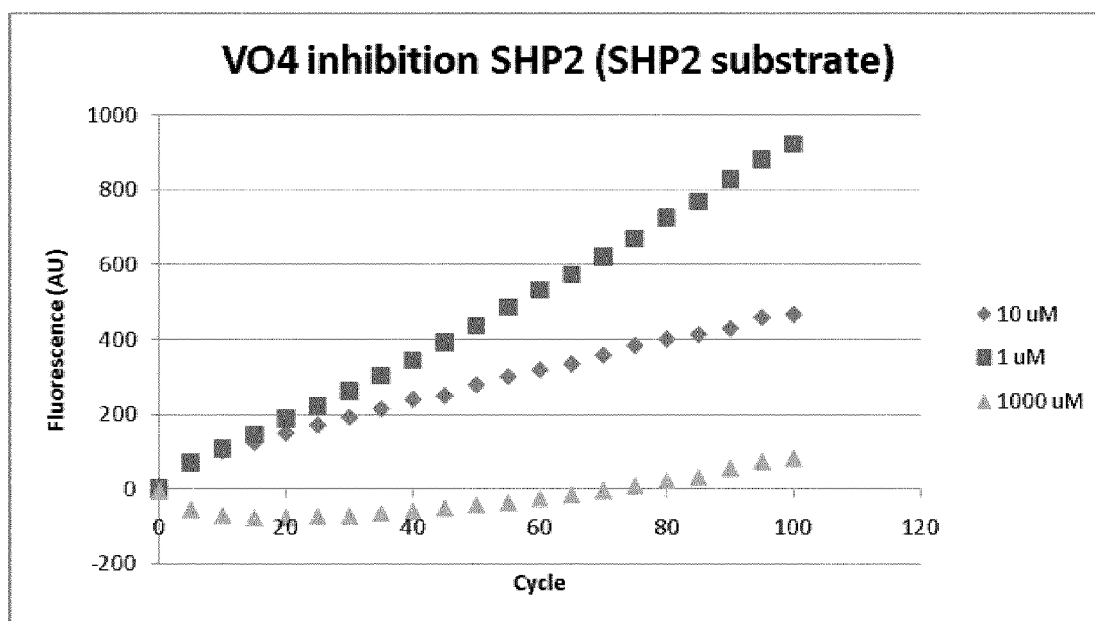
FIG. 5 provides vanadate inhibition profiles.

In order to determine whether the signal obtained was indeed due to phosphatase activity, the non-specific phosphatase inhibitor sodium ortho-vanadate was added and showed concentration dependent inhibition of the phosphatase enzyme activity (FIG. 5).

Figure 6:
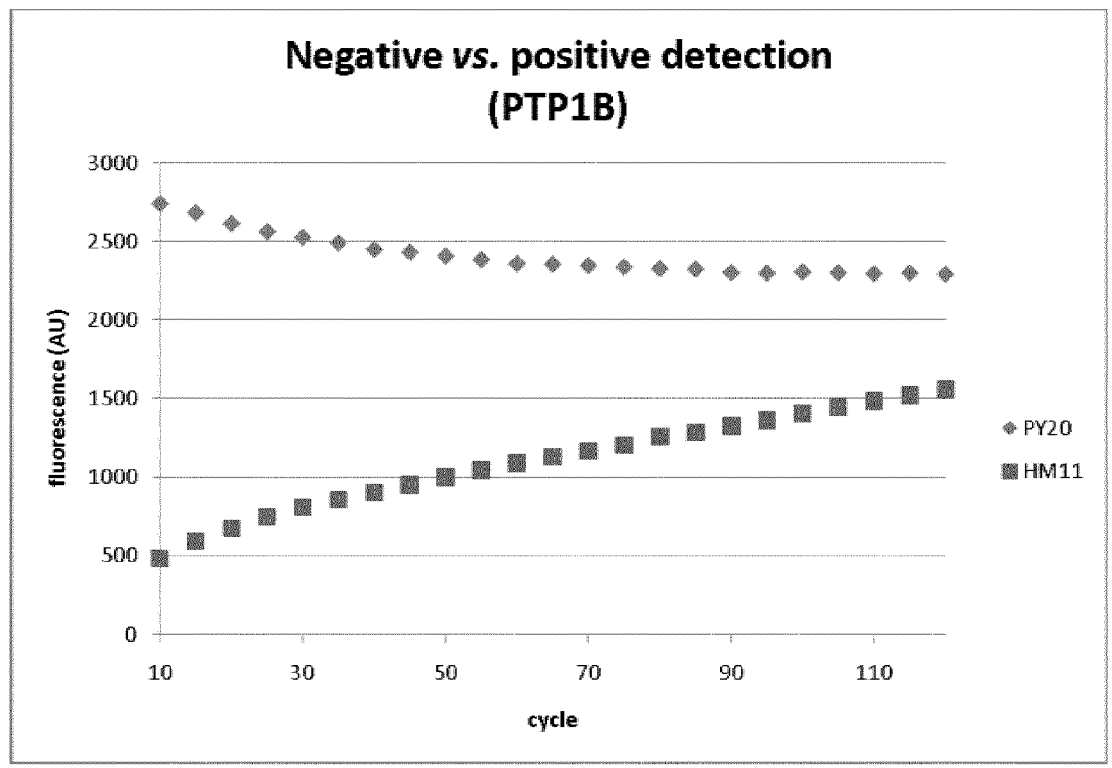
FIG. 6 provides a comparison of detection strategies.

It was found that commercial monoclonal anti-phosphotyrosine antibody PY20 was capable of recognizing 3-nitro-phosphotyrosine as well. Therefore, it was possible to compare monitoring a decreasing signal due to substrate consumption and an increasing signal due to product formation (FIG. 6). As can be seen, the dynamic range and sensitivity are significantly greater in the product formation case, demonstrating the utility of the approach described here.

Figure 7:
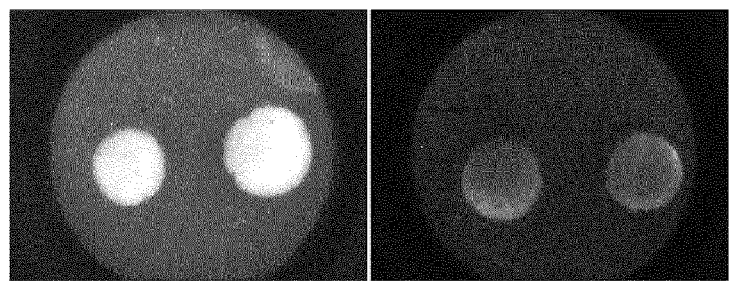
FIG. 7 provides dephosphorylation of 3-bromo-phosphotyrosine derivative.

The 3-bromo-phosphotyrosine peptide was evaluated as well. In this case, it was tested whether a phosphatase could recognize it as a substrate by incubating a microarray surface spotted with a 1 mM solution of the peptide and a 1 mM solution of the corresponding unmodified phosphotyrosine peptide. After one hour incubation with phosphatase PTP1B in a Tris-buffer containing DTT, the microarray was washed and treated with a solution of PY20 antibody. From FIG. 7 it is clear that both peptides were recognized by the phosphatase and dephosphorylated equally well. The left image: not treated with PTP1B. The right image: treated with PTP1B. The left spot: phosphotyrosine peptide. The right spot: 3-bromo-phosphotyrosine peptide.

Figure 8:
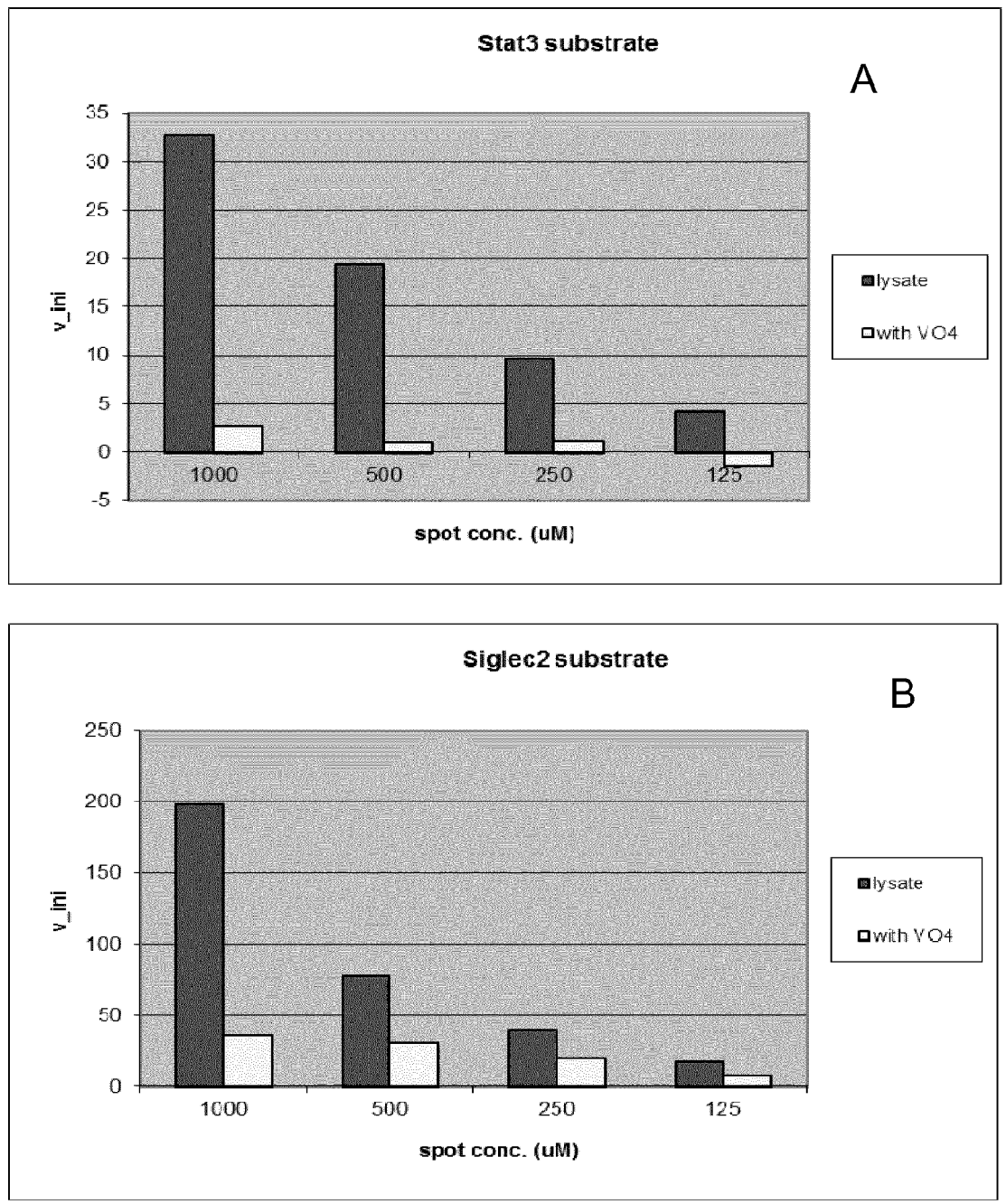
FIG. 8 provides kinetic data in a lysate.

In addition, it was found that is was possible to detect phosphatase activity in a lysate obtained from lysis of HEK 293 cells under normal conditions except for the absence of phosphatase inhibitors. As an example, in FIG. 8 are shown kinetic data for the treatment of a microarray with a cell lysate obtained from HEK 293 cells transfected with the PTP1B gene. Furthermore, an experiment was carried out with the same cell lysate but in the presence of generic phosphatase inhibitor sodium orthovanadate in a concentration of 100 μM. From the combined data, it is clear that the signal monitored was due to the presence of phosphatase activity.

Example 3

Synthesis Fmoc-3-nitrotyrosine allyl ester 2

3-Nitrotyrosine.HNO$_3$ salt (2.89 g, 10 mmol) was suspended in a mixture of dioxane (50 mL) and water (50 mL), after which Fmoc-OSu (3.37 g, 10 mmol) was added. DiPEA was added dropwise while monitoring the pH until this remained stable at 8.5. EtOAc (50 mL) and 1M HCl (50 mL) were added, and the organic layer separated. After drying on Na$_2$SO$_4$ and evaporation of the solvents, the crude material was redissolved in DMF (50 mL) and cooled to 0° C. After addition of DiPEA (1.74 mL, 10 mmol) and allyl bromide (865 μL, 10 mmoL), the reaction mixture was stirred overnight at room temperature. The solvent was evaporated and the crude material redissolved in EtOAc (50 mL), washed with 1M HCl (50 mL) and brine (50 mL), and dried on Na$_2$SO$_4$. After evaporation of the solvents, the crude material was recrystallized from EtOH, yielding the product (4.51 g, 92%) as bright-yellow needles.

Example 4a

Synthesis Fmoc-3-nitro-O-(dibenzylphosphoryl)tyrosine allyl ester 3

Fmoc-3-nitrotyrosine allyl ester 2 (1.91 g, 3.90 mmol) was dissolved in dry THF (50 mL) after which tetrazole (0.82 g, 11.7 mmol) and dibenzyl diisopropylphosphoramidate (2.00 g, 5.8 mmol) were added. The resulting mixture was stirred for 3 h at room temperature, then cooled to 0° C. after which 70-75% mCPBA (1.43 g, 5.8 mmol) was added. After stirring for 10 min at 0° C., EtOAc (50 mL) was added, and this solution washed with water, 1M KHSO$_4$, satd. NaHCO$_3$ and brine (50 mL each). After drying on Na$_2$SO$_4$ and column chromatography (EtOAc/hexanes, 2/3 v/v), the product (2.12 g, 73%) was obtained as a clear, light yellow oil.

Example 4b

Alternative synthesis Fmoc-3-nitro-O-(dibenzylphosphoryl) tyrosine allyl ester 3

An Alternative synthesis method for Fmoc-3-nitro-O-(dibenzylphosphoryl) tyrosine allyl ester 3 starts by dissolving N-chlorosuccinimide (881 mg, 6.6 mmol) in dry THF (30 mL) and cooling to 0° C., after which dibenzylphosphite (1.57 g, 6.0 mmol) was added in portions. The resulting solution was stirred for 2 h at room temperature during which time a white precipitate formed which was removed by filtration. To the resulting clear solution, Fmoc-3-nitrotyrosine allyl ester 2 (2.20 g, 4.5 mmol) and N,N-dimethylaminopyridine (81 mg, 0.5 mmol) were added. After dropwise addition of a solution of triethylamine (836 μL, 6.0 mmol) in dry THF (10 mL), the reaction mixture was stirred for 3 h at room temperature. 1M HCl was added and the product extracted with EtOAc, and subsequently dried on $Na_2SO_4$. Column chromatography (EtOAc/hexanes, 1/2 v/v) afforded the product (2.04 g, 61%) as a clear, light yellow oil.

Example 5

Synthesis
Fmoc-3-nitro-O-(dibenzylphosphoryl)tyrosine 4

Synthesis Fmoc-3-nitro-O-(dibenzylphosphoryl)tyrosine allyl ester 3 (3.15 g, 4.2 mmol) was dissolved in dry THF (20 mL), after which N-methylaniline (1.40 mL, 12.9 mmol) and tetrakis triphenylphosphine palladium (254 mg, 0.22 mmol) were added. After stirring for 2 h at room temperature under a $N_2$-atmosphere in the dark, EtOAc (50 mL) and 1M $KHSO_4$ (50 mL) were added. After drying on $Na_2SO_4$ and column chromatography (5% MeOH in DCM), the product (2.72 g, 91%) was obtained as a light yellow foam.

Example 6

Synthesis Fmoc-3-bromotyrosine Pac ester 6

3-Bromotyrosine (8.83 g, 25.9 mmol) and Fmoc-OSu (8.74 g, 25.9 mmol) were suspended in a mixture of dioxane (50 mL) and water (50 mL) after which the pH was kept at 8.5 using DiPEA. After stirring at room temperature for 1 h, the pH was adjusted to 2 with 1M $KHSO_4$ and the product extracted with EtOAc (100 mL). After drying on $Na_2SO_4$, the solvents were evaporated and the residue redissolved in dry EtOAc (250 mL). After cooling to 0° C., triethylamine (3.97 mL, 28.5 mmol) and Pac-bromide (5.67 g, 28.5 mmol) were added, and the resulting mixture stirred at room temperature overnight. After washing with 1M $KHSO_4$ (100 mL), drying on $Na_2SO_4$ and crystallization from EtOAc/hexanes (1/3 v/v), the product (13.7 g, 88%) was obtained.

Example 7

Fmoc-3-bromo-O-(dibenzylphosphoryl)tyrosine Pac ester 7

Fmoc-3-bromotyrosine Pac ester 6 (6.45 g, 10.7 mmol) was dissolved in dry THF (100 mL) after which tetrazole (2.25 g, 32.1 mmol) and dibenzyl diisopropylphosphoramidate (5.32 g, 16.1 mmol) were added. The resulting mixture was stirred for 1 h at room temperature, then cooled to 0° C. after which 70-75% mCPBA (4.00 g, 16.1 mmol) was added. After stirring for 10 min at 0° C., EtOAc (100 mL) was added, and this solution washed with water, 1M $KHSO_4$, satd. $NaHCO_3$ and brine (100 mL each). After drying on $Na_2SO_4$ and column chromatography (EtOAc/hexanes, 1/2 v/v), the product (6.24 g, 68%) was obtained as a clear, colourless oil.

Example 8

Synthesis
Fmoc-3-nitro-O-(dibenzylphosphoryl)tyrosine 8

Fmoc-3-bromo-O-(dibenzylphosphoryl)tyrosine Pac ester 7 (6.22 g, 7.23 mmol) was dissolved in a mixture of water (8 mL), acetic acid (40 mL) and EtOAc (16 mL), after which Zn-dust (2.3 g) was added. The resulting mixture was stirred at 60° C. for 4 h, followed by addition of diethylether (100 mL) and water (50 mL). The organic layer was washed with 1M $KHSO_4$ and brine (50 mL each) and dried on $Na_2SO_4$. After column chromatography (4% MeOH in DCM), the product (4.15 g, 77%) was obtained as a white foam.

Example 9

Synthesis Fmoc-3-aminotyrosine allyl ester 9

3-Nitro derivative 2 (4.11 g, 8.41 mmol) was suspended in a mixture of methanol (25 mL) and acetic acid (25 mL) after which Zn-dust (2.20 g) was added. The resulting mixture was stirred for 1 h at 50° C., and subsequently filtered over Celite®. The solvents were evaporated and the residue redissolved in DCM (50 mL), washed with water (50 mL) and dried on $Na_2SO_4$. Column chromatography (EtOAc/hexanes, 1/1 v/v) yielded the product (2.20 g, 57%) as a pink foam.

Example 10

Synthesis Fmoc-3-azidotyrosine allyl ester 10

3-Amino derivative 9 (2.20 g, 4.8 mmol) was dissolved in a mixture of methanol (20 mL) and water (10 mL), to which $CuSO_4$ (7.2 mg, 45 μmol) was added. The pH was adjusted to 8.5 with $K_2CO_3$, and a solution of $TfN_3$ (7.2 mmol) in DCM added, after which the mixture was stirred overnight at room temperature. EtOAc (50 mL) and 1M HCl (50 mL) were added, and the organic layer dried on $Na_2SO_4$. After column chromatography (EtOAc/hexanes, 1/2 v/v), the product (637 mg, 27%) was obtained as a clear, colourless oil.

Example 11

Synthesis
Fmoc-3-azido-O-(dibenzylphosphoryl)tyrosine allyl ester 11

Fmoc-3-azidotyrosine allyl ester 10 (0.64 g, 1.31 mmol) was dissolved in dry THF (10 mL) after which tetrazole (0.42 g, 6.0 mmol) and dibenzyl diisopropylphosphoramidate (0.69 g, 2.0 mmol) were added. The resulting mixture was stirred for 1 h at room temperature, then cooled to 0° C. after which 70-75% mCPBA (0.39 g, 1.6 mmol) was added. After stirring for 10 min at 0° C., EtOAc (30 mL) was added, and this solution washed with water, 1M $KHSO_4$, satd. $NaHCO_3$ and brine (30 mL each). After drying on $Na_2SO_4$ and column chromatography (EtOAc/hexanes, 2/3 v/v), the product (989 mg, 99%) was obtained as a clear, colourless oil.

Example 12

Synthesis
Fmoc-3-azido-O-(dibenzylphosphoryl)tyrosine 12

Fmoc-3-azido-O-(dibenzylphosphoryl)tyrosine allyl ester 11 (969 mg, 1.30 mmol) was dissolved in dry THF (10 mL), after which N-methylaniline (0.42 mL, 3.9 mmol) and tetrakis triphenylphosphine palladium (75 mg, 0.065 mmol) were added. After stirring for 2 h at room temperature under a $N_2$-atmosphere in the dark, EtOAc (30 mL) and 1M $KHSO_4$ (30 mL) were added. After drying on $Na_2SO_4$ and column chromatography (3% MeOH in DCM), the product (386 mg, 42%) was obtained as a white foam.

Example 13

Synthesis of a Modified Phosphatase Substrate

The solid phase syntheses were carried out on TentaGel® S RAM resin on a 0.125 mmol scale.
Fmoc-deprotection: 20% piperidine/NMP (2×8 min, 3 mL), NMP (3×2 min, 3 mL), DCM (3×2 min, 3 mL). Kaisertest positive.
Coupling regular aminoacid: 0.50 mmol Fmoc-AA, 0.50 mmol BOP, 1.0 mmol DiPEA in NMP (30 min, 3 mL), NMP (3×2 min, 3 mL), DCM (3×2 min, 3 mL). Kaisertest negative.
Coupling modified tyrosine residue: 0.25 mmol Fmoc-AA, 0.50 mmol BOP, 1.0 mmol DiPEA in NMP (1 h, 3 mL), NMP (3×2 min, 3 mL), DCM (3×2 min, 3 mL). Kaisertest negative.
Cleavage and deprotection: 95/2.5/2.5 v/v/v TFA/TIS/$H_2O$ (5 h, 5 mL), precipitation from cold MTBE/hexanes (1/1 v/v), pallet washed three times with diethyl ether, residue lyophilized and purified by RP-HPLC (gradient from 95/5/0.1 v/v/v $H_2O$/acetonitrile/TFA to 95/5/0.1 v/v/v acetonitrile/$H_2O$/TFA, 60 min, Altima C8 column).

Example 14

Phosphatase Assay for 3-Nitro Peptides

A Tris buffer (25 μL, 50 mM, pH 7.4, modified with 0.5 mM DTT) was used to dissolve the appropriate phosphatase (20-100 ng) together with BSA (0.25 μL, 10 mg/mL), anti-nitrotyrosine antibody (0.5 μL, 0.5 mg/mL in PBS pH 7.4), FITC-goat-anti-mouse antibody (0.5 μL, 4 μg/mL). The resulting mixture was added to Pamchip® microarrays and the fluorescence imaged in real time using a Pamstation® PS12 instrument. The images were analyzed using the Bionavigator software package (Pamgene International BV, 's-Hertogenbosch, The Netherlands).

Example 15

Vanadate Inhibition

To the mixture described in Example 14, a 1 μL amount of sodium vanadate solutions with appropriate concentration was added. Data acquisition and processing as described in Example 14.

Example 16

Comparison Monitoring Substrate Consumption and Product Formation

One microarray was treated with the PTP1B phosphatase as described in Example 14, another one with a comparable mixture in which the antibodies were replaced by PY20 (0.2 μL, 1 mg/mL) and water (0.8 μL). Data acquisition and processing as described in Example 14.

Example 17

Measuring Phosphatase Activity in a Lysate

One microarray was treated with 5 μL of a lysate of cells transfected with the PTP1B gene, prepared in absence of phosphatase inhibitors. In one batch sodium orthovanadate was added to a final concentration of 100 uM. For the rest, the assay mixture was composed as described in Example 14. Data acquisition and processing as described in Example 14.

Example 18

Microarray Preparation

Peptides derived from endogenous phosphatase substrates and comprising 3-nitro-phosphotyrosine were spotted onto PamChip® arrays (Pamgene International Ltd., 's-Hertogenbosch, The Netherlands), which are themselves based on Anopore alumina membranes (Whatman, Maidstone, UK) functionalized with a spacer terminating in thiol reactive reactive group. A Scienion SciFlexArrayer S11 spotter was used to spot 300 pL of each premade, centrifuged (3200 rpm, 5 min.) solution of the individual substrates in MQ water in the presence of 1 mM TCEP. The resulting full arrays were dried for 5 min. at 20° C. After spotting, remaining thiol reactive functionalities were inactivated by washing consecutively with 10 mM thiol-PEG (Mercachem, Nijmegen, The Netherlands) in PBS buffer, PBS buffer and MQ water. The final arrays were dried for 10 min. at 20° C. A quality control was carried out where a full array was stained with SYPRO® Ruby (Bio-Rad Laboratories, Hercules Calif., USA) to quantify peptide immobilization for all spots.

Example 19

Activity Profiling Protein Tyrosine Phosphatase Gamma (PTPγ)

Figure 9:
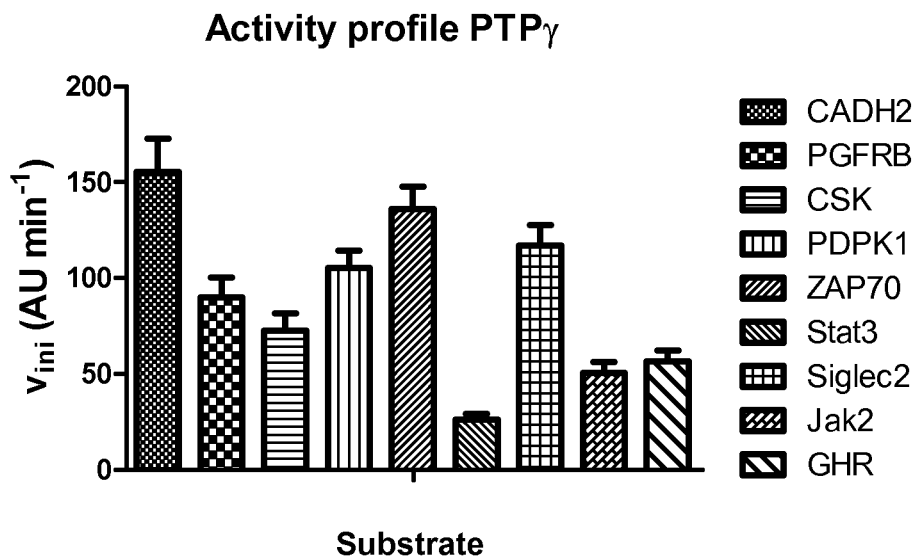
FIG. 9 provides the activity profile of Protein Tyrosine Phosphatase Gamma (PTPγ).

A phosphate buffer (25 μL, 25 mM, pH 7.4, modified with 50 mM NaCl, 5 mM EDTA and 1 mM DTT), was used to dissolve recombinant PTPγ (0.5 mU) together with BSA (0.25 μL, 10 mg/mL), anti-nitrotyrosine (mouse) antibody (0.5 μL, 0.5 mg/mL in PBS pH 7.4), FITC-goat-anti-mouse antibody (0.5 μL, 4 μg/mL) and either additional factors, such as an ortho-vanadate solution, or water. The resulting mixture was added to Pamchip® microarrays and the fluorescence imaged in real time using a Pamstation® 12 instrument. The images were analyzed using the Bionavigator software package (Pamgene International BV, 's-Hertogenbosch, The Netherlands): after automated gridding of the spots, the total fluorescence intensity of each spot was corrected for background fluorescence and the resulting corrected intensity vs. cycle progress curves were fitted to the Michaelis-Menten time course rate equation. The $v_{ini}$ was then calculated as the reaction speed at t=5 cycles for each substrate. The resulting profile is shown in FIG. 9.

Example 20

Activity Profiling of HEK293 Lysate

Figure 10:
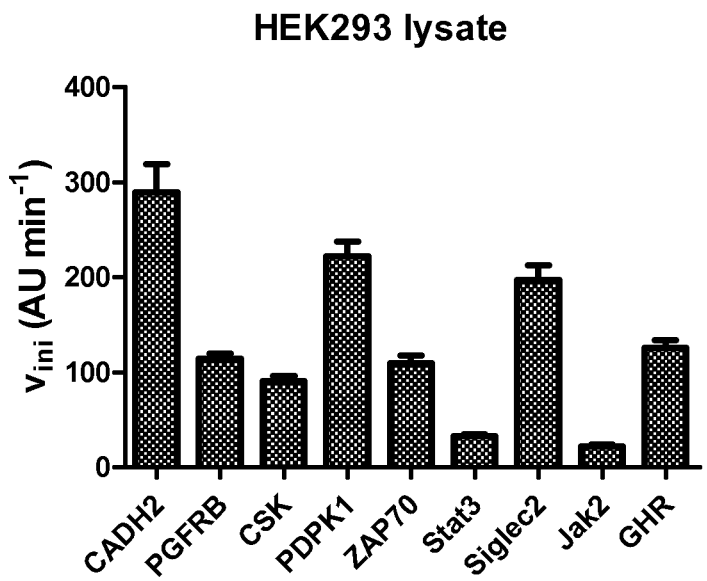
FIG. 10 provides the activity profile of a HEK293 lysate.

Microarrays were first washed with 2% BSA (aq.) for 15 minutes. A suitable volume of HEK293 lysate (corresponding to 1 μg total protein) was used, to which 2.5 μL 10× strength PTP buffer was added in combination with the remaining factors as described above in the general procedure for recombinant PTPs. In the case of the spiked lysate, a solution of purified recombinant PTP1B was added equal to 1 mU as judged by the para-nitrophenylphosphate test. In the vanadate inhibition experiments, a sufficient amount of a 1M sodium ortho-vanadate solution which was heated to 95° C. for 10 minutes prior to uses was added to reach a final concentration of 250 μM. Finally, sufficient water was added to obtain a final volume of 25 μL. Data analysis was carried out as described above for the recombinant PTPs, resulting in the $v_{ini}$ data shown in FIG. 10.

The invention claimed is:

1. A method for detecting hydrolase enzyme activity in a sample, said method comprising the step of:

contacting said sample with one or more modified tyrosine amino acids according to formula IV

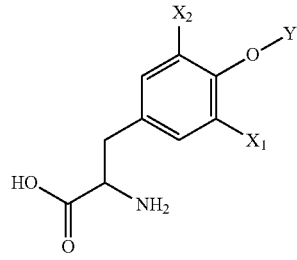

(IV)

wherein Y is chosen from $-PO_y^{2-}$ with y equal to 2 or 3 and esters thereof; and wherein $X_1$ and/or $X_2$ is selected from $-N_3$, $-NO_2$, $-Br$, or H, wherein either $X_1$ or $X_2$ is not H; or contacting said sample with one or more synthetic peptides comprising between 2 and 100 amino acids, characterized therein that said peptide has incorporated therein at least one of said modified tyrosine amino acids detecting the product of the hydrolase enzyme activity on said amino acids or peptides, and optionally detecting the inhibition of hydrolase enzyme activity on said amino acids or peptides.

2. The method according to claim 1 wherein said hydrolase enzyme activity is phosphatase activity and wherein said modified tyrosine amino acids or synthetic peptides comprise at least one nitro phosphate tyrosine residue.

3. The method according to claim 1 wherein said hydrolase enzyme activity is selected from the group consisting of EC 3.1, EC 3.2 and EC 3.3.

4. The method according to claim 1, wherein Y is $-PO_3^{2-}$.

5. The method according to claim 1, wherein $X_1$ is $-NO_2$.

* * * * *

```
                         SEQUENCE LISTING

<160> NUMBER OF SEQ ID NOS: 5

<210> SEQ ID NO 1
<211> LENGTH: 11
<212> TYPE: PRT
<213> ORGANISM: Artificial Sequence
<220> FEATURE:
<223> OTHER INFORMATION: Peptide derived from Stat3, target phosphatase
      PTP1B
<220> FEATURE:
<221> NAME/KEY: MOD_RES
<222> LOCATION: (7)..(7)
<223> OTHER INFORMATION: 3-NO2-phosphotyrosine

<400> SEQUENCE: 1

Cys Gly Ser Ala Ala Pro Tyr Leu Lys Thr Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Peptide derived from Siglec2, target
      phosphatase SHP1
<220> FEATURE:
<221> NAME/KEY: MOD_RES
<222> LOCATION: (8)..(8)
<223> OTHER INFORMATION: 3-NO2-phosphotyrosine

<400> SEQUENCE: 2

Cys Gly Asp Glu Gly Ile His Tyr Ser Glu Leu Ile
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Peptide derived from Jak2, target phosphatase
      SHP2
<220> FEATURE:
<221> NAME/KEY: MOD_RES
<222> LOCATION: (8)..(8)
<223> OTHER INFORMATION: 3-NO2-phosphotyrosine

<400> SEQUENCE: 3

Cys Gly Pro Gln Asp Lys Glu Tyr Tyr Lys Val Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Peptide derived from Stat3, target phosphatase
      PTP1B
<220> FEATURE:
<221> NAME/KEY: MOD_RES
<222> LOCATION: (7)..(7)
<223> OTHER INFORMATION: 3-N3-phosphotyrosine

<400> SEQUENCE: 4
```

```
Cys Gly Ser Ala Ala Pro Tyr Leu Lys Thr Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Peptide derived from EGFR, target phosphatase
      PTP1B
<220> FEATURE:
<221> NAME/KEY: MOD_RES
<222> LOCATION: (6)..(6)
<223> OTHER INFORMATION: 3-Br-phosphotyrosine

<400> SEQUENCE: 5

Cys Asp Ala Asp Glu Tyr Leu Ile Pro Gln Gln Gly
1               5                   10
```